US010947220B2

(12) United States Patent
Abdel-Meguid et al.

(10) Patent No.: US 10,947,220 B2
(45) Date of Patent: Mar. 16, 2021

(54) ANTI-PROPROTEIN CONVERTASE SUBTILISIN KEXIN TYPE 9 (ANTI-PCSK9) COMPOUNDS AND METHODS OF USING THE SAME IN THE TREATMENT AND/OR PREVENTION OF CARDIOVASCULAR DISEASES

(71) Applicant: Shifa Biomedical Corporation, Malvern, PA (US)

(72) Inventors: Sherin Salaheldin Abdel-Meguid, Exton, PA (US); Nabil A. Elshourbagy, West Chester, PA (US); Harold V. Meyers, Weston, MA (US); Shaker A. Mousa, Wynantskill, NY (US)

(73) Assignee: SHIFA BIOMEDICAL CORPORATION, Malvern, PA (US)

( * ) Notice: Subject to any disclaimer, the term of this patent is extended or adjusted under 35 U.S.C. 154(b) by 0 days.

(21) Appl. No.: 16/867,777

(22) Filed: May 6, 2020

(65) Prior Publication Data

US 2020/0262822 A1   Aug. 20, 2020

Related U.S. Application Data

(62) Division of application No. 16/308,648, filed as application No. PCT/US2017/038069 on Jun. 19, 2017.

(60) Provisional application No. 62/352,701, filed on Jun. 21, 2016.

(51) Int. Cl.

| C07D 307/80 | (2006.01) |
| C07D 405/12 | (2006.01) |
| C07D 413/12 | (2006.01) |
| A61K 31/343 | (2006.01) |
| A61K 31/4035 | (2006.01) |
| A61P 3/06 | (2006.01) |

(52) U.S. Cl.
CPC .......... *C07D 405/12* (2013.01); *A61K 31/343* (2013.01); *A61K 31/4035* (2013.01); *A61P 3/06* (2018.01); *C07D 307/80* (2013.01); *C07D 413/12* (2013.01)

(58) Field of Classification Search
CPC ..... C07D 413/12; A61P 3/06; A61K 31/4035; A61K 31/343
See application file for complete search history.

(56) References Cited

U.S. PATENT DOCUMENTS

| 4,017,313 | A | 4/1977 | Hartzler |
| 4,371,607 | A | 2/1983 | Donges |
| 8,003,654 | B2 | 8/2011 | Aissaoui |
| 9,682,085 | B2 | 6/2017 | Abdel-Meguid et al. |
| 2003/0149081 | A1 | 8/2003 | Zou et al. |
| 2008/0090829 | A1 | 4/2008 | Hamanaka |
| 2009/0226422 | A1 | 9/2009 | Chaudhary et al. |
| 2009/0264414 | A1 | 10/2009 | Andersen et al. |
| 2009/0275053 | A1 | 11/2009 | Horton et al. |
| 2010/0184730 | A1 | 7/2010 | Vu et al. |
| 2010/0233177 | A1 | 9/2010 | Yowe et al. |
| 2011/0009628 | A1 | 1/2011 | Liu et al. |
| 2012/0252796 | A1 | 10/2012 | Pingali et al. |
| 2014/0093513 | A1 | 4/2014 | Milne et al. |
| 2014/0099333 | A1 | 4/2014 | Schwink et al. |

FOREIGN PATENT DOCUMENTS

| WO | WO-9827108 A2 * | 6/1998 | ........... C07D 401/12 |
| WO | 2014/150326 A1 | 9/2014 | |

OTHER PUBLICATIONS

U.S. Appl. No. 16/308,648, filed Jun. 2017, Abdel-Meguid.*
STN Registry No. 1287640-99-6 [Entered STN: Apr. 29, 2011]. (Year: 2011).*
STN Registry No. 1011097-75-8 [Entered STN: Mar. 31, 2008]. (Year: 2008).*
Chemical Abstract Service, STN Database, Registry No. 1794134-13-6 [Entered STN: Jul. 5, 2015]. (Year: 2015).*
PUBCHEM ID 798878 (2005) U.S. National Library of Medicine.
PUBCHEM ID 24599432 (2008) U.S. National Library of Medicine.
PUBCHEM ID 1369939 (2005) U.S. National Library of Medicine.
PUBCHEM ID 24404093 (2008) U.S. National Library of Medicine.
Abifadel, M., et al., "Mutations in PCSK9 cause autosomal dominant hypercholesterolemia", Nature Genetics (2003) 34(2):154-156.
Benjannet, S., et al., "The Proprotein Convertase (PC) PCSK9 Is Inactivated by Furin and/or PC5/6A", Journal of Biological Chemistry (2006) 281(41):30561-30572.
Benjannet, S., et al., "NARC-1/PCSK9 and Its Natural Mutants", The Journal of Biological Chemistry (2004) 279(47):48865-48875.
Bottomley, M. J., et al., "Structural and Biochemical Characterization of the Wild Type PCSK9-EGF (AB) Complex and Natural Familial Hypercholesterolemia Mutants", Journal of Biological Chemistry (2009) 284(2):1313-1323.
Cohen, J., et al., "Low LDL cholesterol in individuals of African descent resulting from frequent nonsense mutations in PCSK9", Nature Genetics (2005) 37(2):161-165.
Crunkhorn, S., "PCSK9 antibody reduces LDL cholesterol", Nature Reviews/Drug Discovery (2012) 11:11.
Cunningham, D., et al., "Structural and biophysical studies of PCSK9 and its mutants linked to familial hypercholesterolemia", Nature Structural & Molecular Biology (2007) 14(5):413-419.
Frank-Kamenetsky, M., et al., "Therapeutic RNAi targeting PCSK9 acutely lowers plasma cholesterol in rodents and LDL cholesterol in nonhuman primates", PNAS (2008) 105(33):11915-11920.

(Continued)

*Primary Examiner* — Amanda L. Aguirre
(74) *Attorney, Agent, or Firm* — Robert C. Netter, Jr.; Dann, Dorfman, Herrell & Skillman

(57) ABSTRACT

Disclosed are compounds that modulate the physiological action of the proprotein convertase subtilisin kexin type 9 (PCSK9), as well as therapeutic methods for use of such compounds to reduce LDL-cholesterol levels and/or for the treatment and/or prevention of cardiovascular disease (CVD), including treatment of hypercholesterolemia.

7 Claims, 16 Drawing Sheets

(56) References Cited

OTHER PUBLICATIONS

Graham, M. J. et al., "Antisense inhibition of proprotein convertase subtilisin/kexin type 9 reduces serum LDL in hyperlipidemic mice", Journal of Lipid Research (2007) 48:763-767.
Grundy, S. M. et al., "Implications of Recent Clinical Trials for the National Cholesterol Education Program Adult Treatment Panel III Guidelines", Circulation (2004) 110:227-239.
Kwon, H. J., et al., "Molecular basis for LDL receptor recognition by PCSK9", PNAS (2008) 105(6):1820-1825.
Li, J., et al., "Secreted PCSK9 promotes LDL receptor degradation independently of proteolytic activity", Biochem. J. (2007) 406:203-207.
Maxwell, K. N., et al., "Adenoviral-mediated expression of PCSK9 in mice results in a low-density lipoprotein receptor knockout phenotype", PNAS (2004) 101(18):7100-7105.
McNutt, M., et al., "Antagonism of Secreted PCSK9 Increases Low Density Lipoprotein Receptor Expression in HepG2 Cells", The Journal of Biological Chemistry (2009) 284(16):10561-10570.
McNutt, M., et al., "Catalytic Activity if Not Required for Secreted PCSK9 to Reduce Low Density Lipoprotein Receptors in HepG2 Cells", Journal of Biological Chemistry (2007) 282(29):20799-20803.
Piper, D. E., et al., "The Crystal Structure of PCSK9: A Regulator of Plasma LDL-Cholesterol", Structure (2007) 15:545-552.
Rashid, S., et al., "Decreased plasma cholesterol and hypersensitivity to statins in mice lacking PCSK9", PNAS (2005) 102(15):5374-5379.
Seidah, N. G., et al., "The secretory proprotein convertase neural apoptosis-regulated convertase 1 (NARC-1): Liver recognition and neuronal differentiation", PNAS (2003) 100(3):928-933.
Swergold, G., et al., Core 2. Epidemiology and Prevention of CV Disease: Physiology, Pharmacology and Lifestyle, Circulation (2010) 122:A23251.

Zhang, D. W., et al., "Binding of Proprotein Convertase Subtilisin/Kexin Type 9 to Epidermal Growth Factor-like Repeat A of Low Density Lipoprotein Receptor Decreases Receptor Recycling and Increases Degradation", Journal of Biological Chemistry (2007) 282(25):18602-18612.
Zhao, Z., et al., "Molecular Characterization of Loss-of-Function Mutations in PCSK9 and Identification of a Compound heterozygote", The American Journal of Human Genetics (2006) 79:514-523.
Pisciotta, L., et al., "Additive effect of mutations in LDLR and PCSK9 genes on the phenotype of familial hypercholesterolemia", Atherosclerosis (2006) 186:433-440.
Amgen, "Ascending Multiple Dose Study to Evaluate the Safety, Tolerability, Pharmacokinetics and Pharmacodynamics of Evolocumab (AMG 145) in Adults with Hyperlipidemia on Stable Doses of a Statin", ClinicalTrials.gov (2010).
Xu, et al., "Targeting zymogen activation to control the matriptase-prostasin proteolytic cascade" J. Med. Chem. (2011) 54(21):7567-78.
Santos, et al., "Familial hypercholesterolaemia: PCSK9 inhibitors are coming" Lancet (2015) 385(9965):307-10.
Yangthara, B., et al., "Small-molecule vasopressin-2 receptor antagonist identified by a g-protein coupled receptor "pathway" screen" Mol. Pharmacol. (2007) 72(1):86-94.
Shattat, G., et al., "The hypolipidemic activity of novel benzofuran-2-carboxamide derivatives in Triton WR-1339-induced hyperlipidemic rats: a comparison with bezafibrate" J. Enzyme Inhib. Med. Chem. (2010) 25(6):751-5.
Al-Hiari, et al., "Antihyperlipidemic properties of novel N-(benzoylphenyl)-5-substituted-1H-indole-2-carboxamides in Triton WR-1339-induced hyperlipidemic rats" Molecules (2011) 16(10):8292-304.
Al-Qirim, et al., "In vivo antihyperlipidemic activity of a new series of N-(benzoylphenyl) and N-(acetylphenyl)-1-benzofuran-2-carboxamides in rats" Arch. Pharm. Chem. Life Sci. (2012) 345(5):401-6.

* cited by examiner

ANTI-PROPROTEIN CONVERTASE SUBTILISIN KEXIN TYPE 9 (ANTI-PCSK9) COMPOUNDS AND METHODS OF USING THE SAME IN THE TREATMENT AND/OR PREVENTION OF CARDIOVASCULAR DISEASES

CROSS-REFERENCE TO RELATED APPLICATIONS

The present application is a divisional application of U.S. patent application Ser. No. 16/308,648, filed Dec. 10, 2018, which is a § 371 application of PCT/US2017/038069, filed Jun. 19, 2017, which in turn claims benefit of U.S. Provisional Patent Application No. 62/352,701, filed Jun. 21, 2016. The entire disclosure of each of the foregoing applications is incorporated by reference herein.

STATEMENT REGARDING FEDERAL SPONSORED RESEARCH OR DEVELOPMENT

The present invention was made with support from the National Heart, Lung and Blood Institute (NHLBI) under SBIR Grant No. HL096167. The U.S. Government has certain rights in this invention.

FIELD OF INVENTION

The present invention relates to compounds that modulate the physiological action of the proprotein convertase subtilisin kexin type 9 (PCSK9), including its interaction with the low density lipoprotein receptor (LDLR). More specifically, the invention relates to compositions comprising small molecule modulators of PCSK9 function and methods of using these modulators as a medicament. The small molecule modulators of PCSK9 function can be used therapeutically to lower LDL-cholesterol levels in blood, and can be used in the prevention and/or treatment of cholesterol and lipoprotein metabolism disorders, including familial hypercholesterolemia, atherogenic dyslipidemia, atherosclerosis, and, more generally, cardiovascular disease (CVD).

BACKGROUND OF INVENTION

Cardiovascular diseases are the leading cause of death, with atherosclerosis being the leading cause of cardiovascular diseases. Atherosclerosis is a disease of the arteries and is responsible for coronary heart disease associated with many deaths in industrialized countries. Several risk factors for coronary heart disease have now been identified: dyslipidemia, hypertension, diabetes, smoking, poor diet, inactivity and stress. Dyslipidemia is elevation of plasma cholesterol (hypercholesterolemia) and/or triglycerides (TGs) or a low high-density lipoprotein (HDL) level that contributes to the development of atherosclerosis. It is a metabolic disorder that is proven to contribute to cardiovascular disease. In the blood, cholesterol is transported in lipoprotein particles, where the low-density lipoprotein (LDL) cholesterol (LDL-C) is considered "bad" cholesterol, while HDL-cholesterol (HDL-C) is known as "good" cholesterol. Lipid and lipoprotein abnormalities are extremely common in the general population and are regarded as a highly modifiable risk factor for cardiovascular disease, due to the influence of cholesterol on atherosclerosis. There is a long-felt significant unmet need with respect to CVD with 60-70% of cardiovascular events, heart attacks and strokes occurring despite the treatment with statins (the current standard of care in atherosclerosis). Moreover, new guidelines suggest that even lower LDL levels should be achieved in order to protect high-risk patients from premature CVD (1).

The establishment of a link between PCSK9 and cholesterol metabolism was rapidly followed by the discovery that selected mutations in the PCSK9 gene caused autosomal dominant hypercholesterolemia (2), suggesting that the mutations confer a gain-of-function (3) by increasing the normal activity of PCSK9. This was supported by the experiment in which wild type and mutant PCSK9 (S127R and F216L) were expressed at high levels in the livers of mice; hepatic LDLR protein levels fell dramatically in mice receiving either the wild type or mutant PCSK9 (4, 5). No associated reductions in LDLR mRNA levels were observed, indicating that overexpression of PCSK9, whether mutant or wild type reduces LDLRs through a post-transcriptional mechanism.

Given that gain-of-function mutations in PCSK9 cause hypercholesterolemia, it was reasonable to ask if loss-of-function mutations would have the opposite effect and result in hypocholesterolemia. Three loss-of-function mutations in PCSK9 (Y142X, L253F, and C679X) were identified in African-Americans (6). These mutations reduce LDL-C levels by 28% and were shown to decrease the frequency of CHD (defined as myocardial infarction, coronary death or coronary revascularization) by 88%. Rashid et al. (7) studied the mechanism of loss-of-function mutations in mice where PCSK9 was inactivated. They reported that these knockout mice showed increased hepatic LDLR protein (but not mRNA), increased clearance of circulating lipoproteins and reduced plasma cholesterol levels. Structure-function relationship analysis of the naturally occurring mutations in PCSK9 has also provided insights into the mechanism of action of PCSK9. Interestingly, mutations in PCSK9 that were found to be associated with the greatest reductions in LDL-C plasma levels are those that prevent the secretion of mature PCSK9 by disrupting its synthesis (Y142X), autocatalytic processing (L253F), or folding (C679X) (8). The Y142X mutation produces no detectable protein because it occurs early in the transcript and is predicted to initiate nonsense-mediated mRNA decay. Mutations in the catalytic domain (L253F) interfere with the autocatalytic cleavage of the protein. In cells expressing the PCSK9-253F, the amount of mature protein was reduced compared to that in cells expressing PCSK9-WT, suggesting that the mutation inhibits autocatalytic cleavage. The L253F mutation is near the catalytic triad (PCSK9 is a serine protease), therefore it might disrupt the active site (8). Inasmuch as autocatalytic cleavage of PCSK9 is required for export of the protein out of the ER, the L253F mutation delays transport of PCSK9 from the ER to the cell surface. The nonsense mutation (C679X) in PCSK9, which truncates the protein by 14 amino acids, did not interfere with protein processing, but the mature protein accumulates in the cells and none is secreted, suggesting that the protein is cleaved normally but is misfolded and is retained in the ER (8, 9).

The mechanism by which PCSK9 causes the degradation of the LDLR has not been fully elucidated. However, it is clear that the protease activity of PCSK9 is not required for LDLR degradation (10, 11). Li et al. (10) have co-expressed the prodomain and the catalytic domain in trans, and showed that the secreted PCSK9 was catalytically inactive, yet it is functionally equivalent to the wild-type protein in lowering cellular LDL uptake and LDLR levels. Similar studies were also reported by McNutt et al. (11). Furthermore, Zhang et al. (12) has mapped PCSK9 binding to the EGF-A repeat of the LDLR, and showed that such binding decreases the receptor recycling and increases its degradation. They also reported that binding to EGF-A domain was calcium-dependent and increased dramatically with reduction in pH from 7 to 5.2. Kwon et al. (13) determined the crystal structure of PCSK9 in complex with the LDLR-EGF-AB (EGF-A and EGF-B). The structure shows a well-defined EGF-A domain, but the EGF-B domain is disordered and absent from their electron density map. The EGF-A domain binds to the PCSK9 catalytic domain at a site distant from the catalytic site, and makes no contact with either the C-terminal domain or the prodomain (14).

Several strategies have been proposed for targeting PCSK9 (15). Strategy 1: mRNA knockdown approaches include the use of antisense oligonucleotides or RNAi. Antisense oligonucleotides administered to mice reduced PCSK9 expression by >90% and lowered plasma cholesterol levels by 53% (16). A single intravenous injection of an RNAi delivered in lipidoid nanoparticles to cynomologous monkeys reduced plasma PCSK9 levels by 70% and plasma LDL-C levels by 56% (17). Strategy 2: is to prevent binding of PCSK9 to the LDLR on the cell surface with a small molecule, a peptide, or an antibody directed against PCSK9. Adding EGF-A fragments to cultured cells inhibits the ability of exogenously added PCSK9 to mediate LDLR degradation. Strategy 3: is to develop small-molecule inhibitors of the PCSK9 processing. Despite evidence that the catalytic activity of PCSK9 is not required for LDLR degradation (11), an intracellular inhibitor of PCSK9 catalytic activity should be effective, since autocatalytic processing of PCSK9 is required for secretion of the protein from the ER. Following its synthesis, PCSK9 undergoes an autocatalytic cleavage reaction that clips off the prodomain, but the prodomain remains attached to the catalytic domain (18, 19). The autocatalytic processing step is required for the secretion of PCSK9 (20), likely because the prodomain serves as a chaperone and facilitates folding. The continued attachment of the prodomain partially blocks the substrate binding pocket of PCSK9 (18, 19). McNutt et al. (21) demonstrated that antagonism of secreted PCSK9 increases LDLR expression in HepG2 cells. They show that an FH-associated LDLR allele (H306Y) that results in a gain-of-function mutation is due to an increase in the affinity of PCSK9 to the LDLR, which would lead to enhanced LDLR destruction, and decreased plasma LDL-C clearance. Furthermore, they were able to show elegantly that blocking the secreted PCSK9 with LDLR (H306Y) sub-fragment resulted in an increase in the level of LDLR in cultured HepG2 cells. Therefore, PCSK9 acts as a secreted factor to cause LDLR degradation, and a small molecule inhibitor that interferes with the autocatalytic process should decrease the amount of mature secreted PCSK9. This invention relates to identification of small molecules that down-regulate the function of PCSK9 using Strategy 2.

Currently (22-24), there are FDA approved injectable PCSK9 monoclonal antibody antagonists on the market. These are Regeneron/Sanofi's PRALUENT (alirocumab) and Amgen's REPATHA (evolocumab), both of which are fully human anti-PCSK9 monoclonal antibodies. Pfizer's bococizumab, which is being developed collaboratively with Halozyme, is furthest ahead at Phase III. Eli Lily's humanized mAb started Phase II trials. These monoclonal antibodies approaches follow Strategy 2 using injectable antibodies instead of small molecules. Strategy 2 is also being pursued by several other companies (25).

SUMMARY OF THE INVENTION

This invention relates to therapeutic applications of small molecules that selectively interact with and down modulate PCSK9 function. In a first embodiment, the agents used in the practice of this invention have the general formula I:

wherein A is selected from the group consisting of:

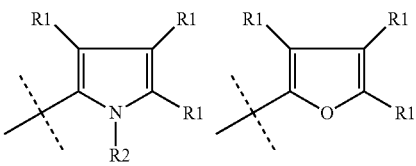

wherein Ra is independently selected from the group consisting of H and lower alkyl; $R_1$ is independently selected from the group consisting of H, halogen, nitro, cyano, hydroxyl, and optionally substituted amino, alkoxy, alkoxycarbonyl, alkoxyalkyl, alkylthio, alkylthioalkyl, acyl, carboxy, amido, aminocarbonyl, monoalkylaminocarbonyl, dialkylaminocarbonyl, monoalkylaminosulfinyl, dialkylaminosulfinyl, monoalkylaminosulfonyl, dialkylaminosulfonyl, alkylsulfonylamino, hydroxysulfonyl, alkoxysulfonyl, alkylsulfonylalkyl, monoalkylaminosulfonylalkyl, dialkylaminosulfonylalkyl, and, optionally substituted, lower alkyl, cycloalkylalkyl, aralkyl, heterocyclylalkyl, heteroarylalkyl, cycloalkyl, alkenyl, alkynyl, aryl, heterocycle, heteroaryl, or taken together with an adjacent $R_1$ forms an optionally substituted 5-7 membered carbocycle, aryl, heterocycle, or heteroaryl. $R_2$ is selected from the group consisting of H and optionally substituted lower alkyl; with the proviso that A is not a 2-substituted indole.

B is selected from the group consisting of optionally substituted cycloalkyl, aryl, heterocycle, and heteroaryl and the pharmaceutically acceptable salts and all stereoisomers of the compound.

In one embodiment, the invention provides a method for the treatment or prophylaxis of hypercholesterolemia and/or at least one symptom of dyslipidemia, atherosclerosis, CVD or coronary heart disease in a patient in need of such treatment comprising administering to such a patient a therapeutically effective amount of a compound of formula I, above.

In another embodiment, the method of the invention involves administration of at least one compound of the following formula II:

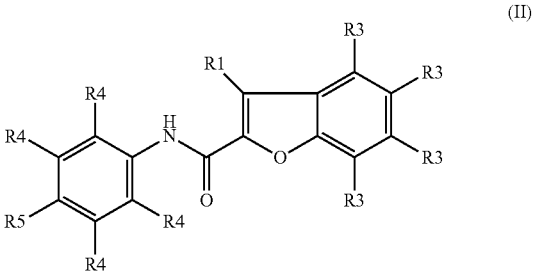

wherein $R_1$ is independently selected from the group consisting of H, and optionally substituted ($C_1$-$C_3$)-alkyl, ($C_1$-$C_3$)-alkoxyalkyl, aryloxyalkyl, ($C_1$-$C_3$)-alkylthioalkyl, arylthioalkyl, aryl, and heteroaryl; $R_3$ is independently selected from the group consisting of H, halogen, nitro, cyano, ($C_1$-$C_3$)-alkoxy, ($C_1$-$C_3$)-alkoxycarbonyl, ($C_1$-$C_3$)-alkoxyalkyl, aryloxyalkyl, ($C_1$-$C_3$)-alkylthio, ($C_1$-$C_3$)-alkylthioalkyl, arylthioalkyl, ($C_1$-$C_3$)-acyl, carboxy, amido, aminocarbonyl, monoalkylaminocarbonyl, dialkylaminocarbonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, and, optionally substituted, lower alkyl, cycloalkylalkyl, aralkyl, heterocyclylalkyl, heteroarylalkyl, cycloalkyl, alkenyl, alkynyl, aryl, heterocycle, heteroaryl or taken together with and adjacent $R_3$ forms an optionally substituted 5-7 membered carbocycle, aryl, heterocycle, or heteroaryl; $R_4$ is independently selected from the group consisting of H, halogen, ($C_1$-$C_3$) alkyl and ($C_1$-$C_3$) alkoxy; $R_5$ is independently selected from the group consisting of H and $CONR_6R_7$, wherein $R_6$ and $R_7$ are independently selected from the group consisting of H and optionally substituted alkyl, cycloalkylalkyl, aralkyl, heterocyclylalkyl, heteroarylalkyl, cycloalkyl, alkenyl, alkynyl, aryl, heterocycle, and heteroaryl, or i) taken together forms an optionally substituted 5-7 membered heterocycle containing one or more heteroatoms; or ii) taken together with an adjacent $R_4$ forms an optionally substituted 5-7 membered heterocycle.

In a more preferred embodiment, the method of the invention involves administration of at least one compound of the following formula III:

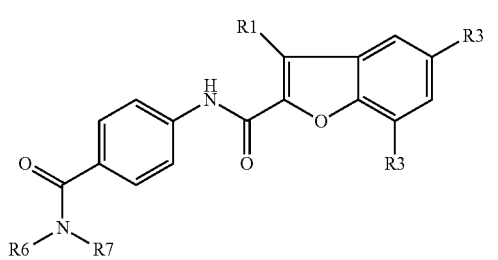

(III)

wherein $R_1$ is independently selected from the group consisting of H or $CH_3$; $R_3$ is independently selected from the group consisting of H, or ($C_1$-$C_3$)-alkoxy; $R_6$ and $R_7$ are independently selected from the group consisting of H, $CH_3$, and optionally substituted aryl, wherein aryl is selected from the group consisting of

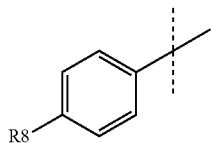

wherein $R_8$ is selected from the group consisting of $CO_2H$, $CONHR_9$, 2-oxazole, 2-oxazoline, 2-benzoxazole; $R_9$ is H or $CH_3$.

In yet another embodiment, the method of the invention involves administration of at least one compound of the following formula IV:

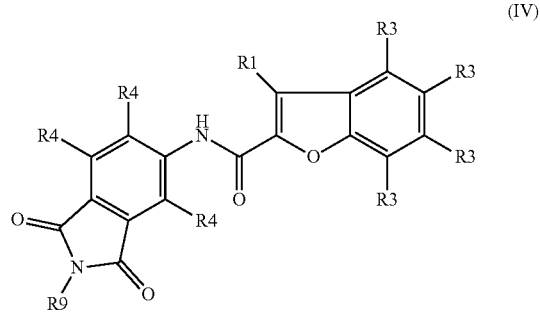

(IV)

wherein $R_1$ is H or optionally substituted ($C_1$-$C_3$)-alkyl; $R_3$ is independently selected from the group consisting of H, halogen, or optionally substituted ($C_1$-$C_3$)-alkoxy; $R_4$ is H; and $R_9$ is ($C_1$-$C_3$)-alkyl.

In a further embodiment, the present invention provides a compound of the formula V:

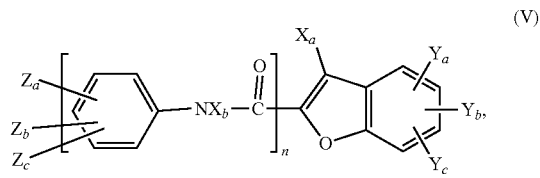

(V)

including pharmaceutically acceptable salts and stereoisomers of said compound, wherein $X_a$ and $X_b$ are independently selected from the group of H or $CH_3$; $Y_a$, $Y_b$ and $Y_c$ may be the same or different and are selected from the group of H, halogen or ($C_1$-$C_3$)-alkoxy; Za, Zb and Zc are the same or different and are selected from the group of H, halogen, ($C_1$-$C_3$)-alkoxy, ($C_1$-$C_4$)-alkyl, COOH, $CONR_{10}R_{11}$, 2-oxazole, 2-oxazoline and 2-benzoxazole; $R_{10}$ and $R_{11}$ are independently selected from the group of H, optionally substituted ($C_1$-$C_3$)-alkyl and optionally substituted aryl; n=1 or 2, and when n=1, $CONR_{10}R_{11}$ may form a N-substituted succinimide ring fused to the benzene ring to which said $CONR_{10}R_{11}$ is attached, wherein the succinimide substituent is optionally substituted ($C_1$-$C_3$) alkyl or aryl, with the proviso that said formula does not include

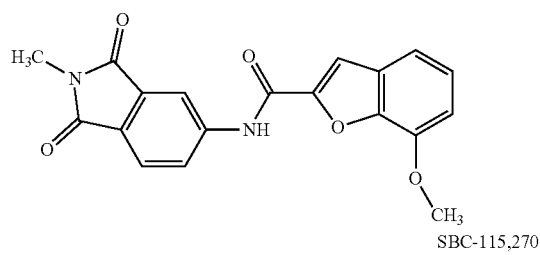

SBC-115,202

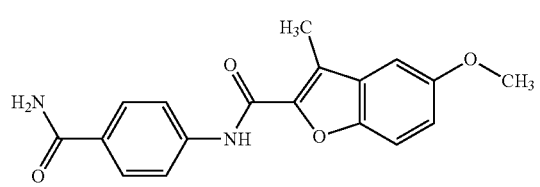

SBC-115,270

-continued

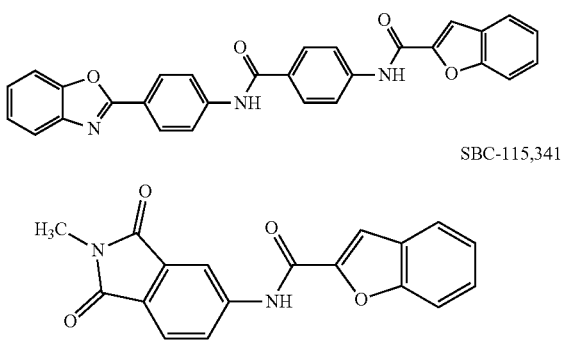

SBC-115,337

SBC-115,341

DESCRIPTION OF DRAWINGS AND TABLES

FIG. 1 sets forth the structure of selected compounds of the formula I, namely 2-carboxanilide pyrroles and 2-carboxanilide indoles, that have an effect on LDLR upregulation as compared to control while having no effect on PCSK9 processing and secretion, and show in vitro inhibition of PCSK9/LDLR interaction at 100 μM>20%. Structures for SBC-115,210, SBC-115,211, SBC-115,228, SBC-115,232, SBC-115,229, SBC-115,230, SBC-115,235, SBC-115,240, SBC-115,242, SBC-115,243, SBC-115,249, SBC-115,293, SBC-115,307, and SBC-115,332 are provided.

FIG. 2 sets forth the structure of preferred compounds of the formula II-IV, namely 2-carboxanilide benzofurans, that have an effect on LDLR upregulation as compared to control while having no effect on PCSK9 processing and secretion, and show in vitro inhibition of the PCSK9/LDLR interaction ($IC_{50}$, μM) >10 μM but ≤50 μM. Structures for SBC-115, 203, SBC-115,251, SBC-115,256, SBC-115,419, SBC-115, 422, SBC-115,425, SBC-115,427, SBC-115,429, SBC-115, 430, SBC-115,435, SBC-115,437, SBC-115,438, SBC-115, 439, SBC-115,440, SBC-115,441, SBC-115,442, SBC-115, 444, and SBC-115,446 are provided.

FIG. 3 sets forth the structure of the most preferred compounds of the formula II-IV that have an effect on LDLR upregulation as compared to control while having no effect on PCSK9 processing and secretion, and show in vitro inhibition of the PCSK9/LDLR interaction ($IC_{50}$, μM)<10 μM. Structures for SBC-115,202, SBC-115,270, SBC-115, 271, SBC-115,337, SBC-115,341, SBC-115,415, SBC-115, 417, SBC-115,418, SBC-115,421, SBC-115,423, SBC-115, 424, SBC-115,426, SBC-115,431, SBC-115,432, SBC-115, 433, SBC-115,436, SBC-115,443, SBC-115,445, and SBC-115,447 are provided.

FIG. 4 shows the effect of different compounds on the PCSK9/LDLR interaction: An in vitro ELISA assay kit was utilized (Circulex). For screening inhibitors of the PCSK9/LDLR interaction, different concentrations (0.01 nM-100 μM) of selected compounds were incubated with His-tagged PCSK9 and then added to wells that were pre-coated with recombinant LDLR-AB domain. After incubation, the plate was washed and the amount of recombinant His-tagged PCSK9 was measured using the biotinylated anti-His-tag and horseradish peroxidase conjugated Streptavidin, and quantitated using a BioTek Synergy 2 plate reader. The effect of each compound on the PCSK9 binding to the recombinant LDLR-AB domain was calculated.

FIG. 5 shows the effect of different compounds on PCSK9 synthesis, processing and secretion in HEK293 transfected cells. HEK-293T cells were seeded into 96 well plates in a DMEM containing 10% Fetal Bovine Serum media and incubated overnight at 37° C. Cells were transiently transfected with cDNA construct using the Lipofectamine-LTX. Compounds (25 μM) or vehicle were added, followed by additional 43 hours of incubation. Cellular PCSK9, secreted PCSK9, and cell viability were analyzed as described in Example 2 below.

FIG. 6 shows increased degradation of the LDLR by PCSK9. HEK-293T cells were seeded in a DMEM containing 10% Fetal Bovine Serum media and incubated overnight at 37° C. Cells were transiently transfected with Mock (lanes 1 and 2), PCSK9 (lanes 3 and 4), LDLR & PCSK9 (lanes 5 and 6), and LDLR (lanes 7 and 8) cDNA constructs using the Lipofectamine-LTX. Cells were incubated for an additional 72 hrs, and cells and media were analyzed as in text.

FIG. 7 shows upregulation of LDLR by PCSK9 antagonists. HEK-293T cells were seeded in a DMEM containing 10% Fetal Bovine Serum media and incubated overnight at 37° C. Cells were transiently transfected with LDLR & PCSK9 cDNA constructs using the Lipofectamine-LTX as described above. After 24 hrs, cells were treated with different compounds and incubated for an additional 48 hrs. Cells were assayed as described above for LDLR expression.

FIG. 8 shows effect of different compounds on LDLR upregulation in HepG2 cells. HepG2 cells were seeded into 96 well plates in a MEM containing 10% Fetal Bovine Serum media and incubated overnight at 37° C. Cells were transiently transfected with PCSK9 cDNA constructs using the Lipofectamine-LTX. Compounds were added, followed by additional 43 hours of incubation. The cells were lysed and analyzed for LDLR expression and cell viability determined as described above.

FIG. 9 shows increased uptake of Fluorescent Dil-LDL using four inhibitors in HepG2 cells. The SBC compounds were validated for their ability to increase uptake of Fluorescent Dil-LDL in HepG2 cells. The data show an increase in the Fluorescent Dil-LDL uptake using 1.2 μM of the compound.

FIG. 10 shows the effect of SBC-115,337 on LDL cholesterol levels of 8 mice fed high fat diet (HFD) with and without LPS compared to animals fed regular diet. C57/Black 6 mice and BalB/C mice were maintained on the HFD for 4 weeks. Blood plasma was collected at day 1 prior to injection of the SBC compounds. Blood plasma was collected at day 4, at 4 hours after the LPS injection, and again at 24 hours after LPS injection. Plasma cholesterol, LDL-C, HDL-C, and triglyceride levels were measured enzymatically.

Figure 1:
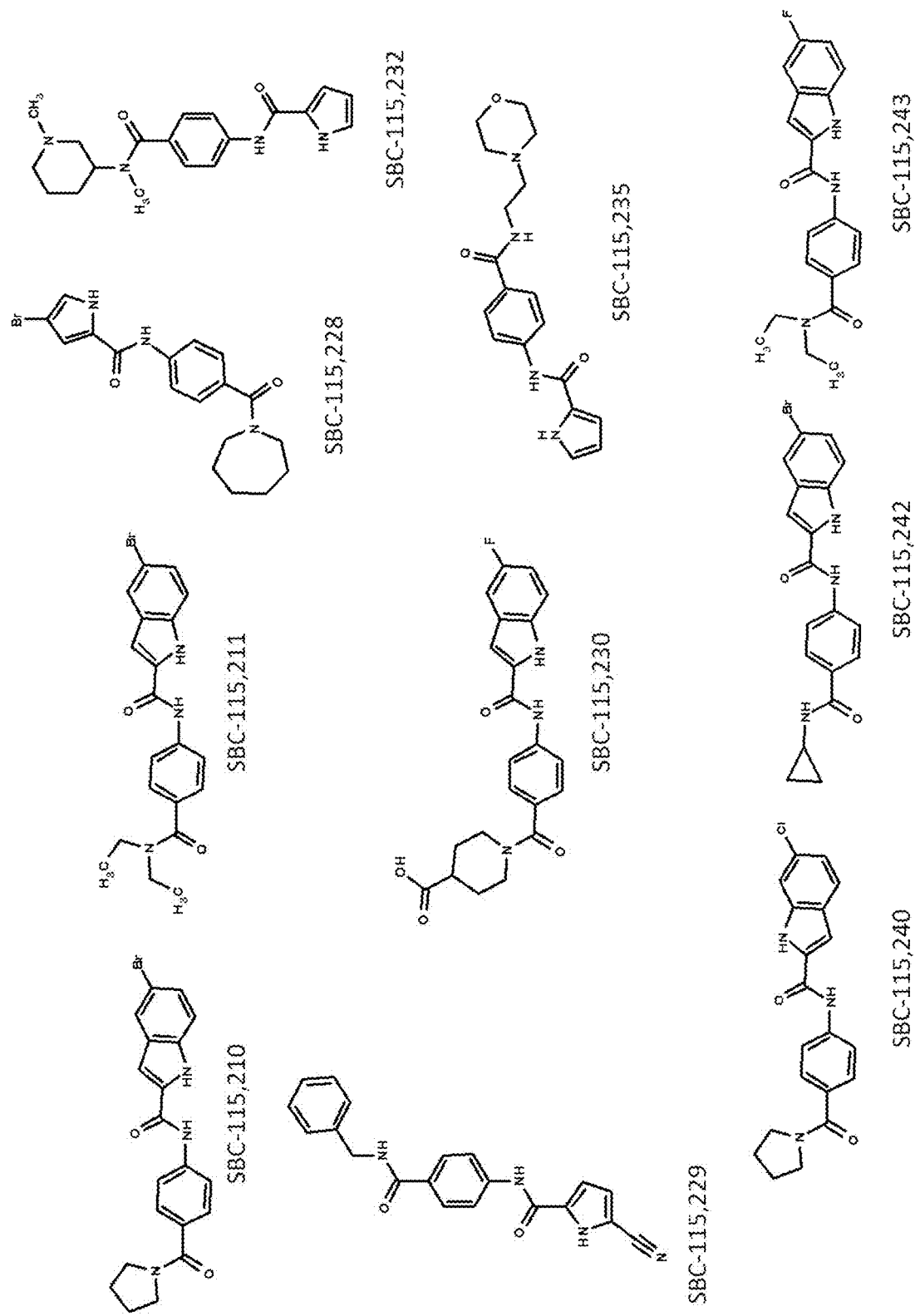
Figure 1:
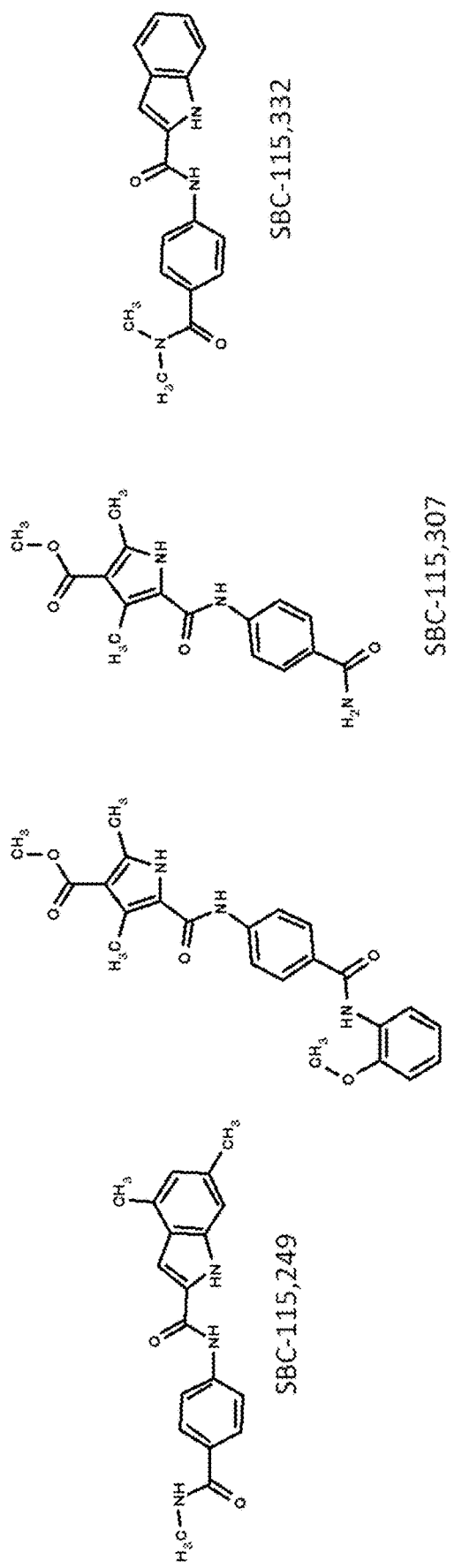

C57BL/6 mice were divided into 2 groups of 5 animals in each; control group received PBS; SBC-group received 10 mg/kg oral daily for 5 days. Blood plasma was collected at day 1 prior to injection of the compounds. Blood plasma was collected again at day 5. Plasma LDL-C levels was measured enzymatically. (FIG. 15A) Representing the actual change in the LDL-C in mg/dL and (FIG. 15B) representing the % reduction of LDL-C after the administration of SBC-115,418 for 5 days.

DETAILED DESCRIPTION OF THE INVENTION

The present invention relates to small molecules that down regulate the function of extracellular proprotein convertase subtilisin kexin type 9 (PCSK9), including its interaction with the low density lipoprotein (LDL) receptor (LDLR), and methods of using these antagonists as a medicament. The small molecule modulators of PCSK9 function can be used therapeutically to lower LDL-cholesterol levels in blood, and can be used in the prevention and/or treatment of cholesterol and lipoprotein metabolism disorders, including familial hypercholesterolemia, atherogenic dyslipidemia, atherosclerosis, and, more generally, cardiovascular disease (CVD).

As used herein, the term "alkyl" is a branched or unbranched saturated hydrocarbon chain moiety. "Lower alkyl" denotes branched or unbranched hydrocarbon chains, having 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group which may be substituted with one or more substituent groups which are attached commonly to such chains, such as, hydroxy, halogen, mercapto or thio, cyano, alkylthio, carboxy, carbalkoxy, amino, nitro, alkoxy, or optionally substituted, alkenyl, alkynyl, heterocyclyl, aryl, heteroaryl, and the like to form alkyl groups such as trifluoro methyl, 3-hydroxyhexyl, 2-carboxypropyl, 2-fluoroethyl, carboxymethyl, cyanobutyl, phenethyl, benzyl and the like.

The term "halogen" or "halo" as used herein alone or as part of another group refers to chlorine, bromine, fluorine, and iodine.

The term "alkoxy" refers to alkyl-O—, in which alkyl is as defined above.

The term "alkylthio" refers to alkyl-S—, in which alkyl is as defined above.

The terms "amino", "monoalkylamino", "dialkylamino" refer to the moiety —NR'R", in which R' and R", each independently represents H, alkyl or aryl, all as defined herein.

The term "carboxy" refers to the moiety —C(=O)OH.

The term "carbalkoxy" refers to the moiety —C(=O)O-alkyl, in which alkyl is as defined above.

The term "amino (monoalkylamino-, dialkylamino-) carbonylamino" refers to the moiety —NHC(=O)NR'R", in which R'R", each independently represents H, alkyl or aryl, all as defined herein.

The term "carbamato" refers to the moiety —NR'C(=O)OR", in which R' and R", each independently represents H, alkyl or aryl, all as defined herein.

The term "amino (monoalkylamino, dialkylamino) carbonyl" (also "carboxamido") refers to the moiety —C(=O)NR'R", in which R' and R" each independently represents H, alkyl, or aryl, all as defined herein.

The term "amido" refers to the moiety —NRC(=O)—R", in which R' and R", each independently represents H, alkyl or aryl, all as defined herein.

The term "alkylsulfonyl" refers to the moiety —S(=O)2-alkyl, in which alkyl is as previously defined.

The term "alkylsulfonyloxy" refers to the moiety —OS(=O)2-alkyl, wherein alkyl is as previously defined.

The term "amino (monoalkylamino-, dialkylamino-) sulfinyl" refers to the moiety —S(=O)NR'R" in which R' and R" each independently represents H, alkyl or aryl, all as defined herein.

The term "amino (monoalkylamino-, dialkylamino-) sulfonyl" refers to the moiety —S(=O)2NR'R", in which R' and R" each independently represents H, alkyl or aryl, all as defined herein.

The term "alkylsulfonylamino" refers to the moiety —NHS(=O)2-alkyl, in which alkyl is as previously defined.

The term "hydroxysulfonyloxy" refers to the moiety —OS(=O)2OH.

The term "alkoxysulfonyloxy" refers to the moiety —OS(=O)2O-alkyl, in which alkyl is as previously defined.

The term "alkylsulfonyloxy" refers to the moiety —OS(=O)2-alkyl, in which alkyl is as previously defined.

The term "hydroxysulfonyl" refers to the moiety —S(=O)2OH.

The term "alkoxysulfonyl" refers to the moiety —S(=O)2O-alkyl, wherein alkyl is as previously defined.

The term "alkylsulfonylalkyl" refers to the moiety -alkyl-S(=O)2-alkyl, wherein alkyl (each instance) is as previously defined.

The term "amino (monoalkylamino-, dialkylamino-) sulfonylalkyl" refers to the moiety -alkyl-S(=O)2-NR'R", wherein alkyl is as previously defined, and R' and R" each independently represents H, alkyl or aryl, all as defined herein.

The term "amino (monoalkylamino-, dialkylamino-) sulfinylalkyl" refer to the moiety -alkyl-S(=O)—NR'R", wherein alkyl is as previously defined, and R' and R" each independently represents H, alkyl or aryl, all as defined herein.

Unless otherwise indicated, the term "cycloalkyl" as employed herein alone or as part of another group includes saturated or partially unsaturated (containing 1 or more double bonds) cyclic hydrocarbon groups (carbocyclic) containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl cyclododecyl and cyclohexenyl.

"Substituted cycloalkyl" includes a cycloalkyl group which may be substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group which may be substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group which may be substituted with one or more substituents, such as the substituents included above in the definition of "substituted alkyl" and "substituted cycloalkyl."

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring, such as a cycloalkyl ring or fused to an aryl or heterocyclic ring or substituted forms thereof.

"Substituted aryl" includes an aryl group which may be substituted with one or more substituent groups, such as halo, alkyl, haloalkyl (e.g., trifluoromethyl), alkoxy, haloalkoxy (e.g., difluoromethoxy), alkenyl, alkynyl, cycloalkyl-alkyl, heterocyclo-alkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonyl, monoalkylaminocarbonyl, dialkylaminocarbonyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents mentioned in the definitions), thiol, alkylthio, heteroarylthio, arylthioalkyl, alkoxyarylthio, alkylaminocarbonyl, arylaminocarbonyl, alkylcarbonyloxy, arylcarbonyloxy, alkylcarbonylamino, arylcarbonylamino, arylsulfinylalkyl, arylsulfonylamino or arylsulfonaminocarbonyl and/or any of the alkyl substituents referred to above.

Unless otherwise indicated, the term "heteroaryl" or "Het" as used herein alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring and includes possible N-oxides. Examples of heteroaryl groups include pyrrolyl, furanyl, thienyl, pyrazolyl, imidazolyl, pyridyl, pyrazinyl, pyrimidinyl, pyridazinyl, oxazolyl, isooxazolyl, thiazolyl, isothiazolyl, thiadiazolyl and oxadiazolyl. Examples of fused heteroaryl groups include quinoline, isoquinoline, indole, isoindole, carbazole, acridine, benzimidazole, benzofuran, benzoxazole, isobenzofuran, benzothiophene, phenanthroline, purine, and the like. "Substituted heteroaryl" includes a heteroaryl group which may be substituted with 1 to 4 substituents, such as the substituents included above in the definition of "substituted alkyl" "substituted cycloalkyl" and "substituted aryl".

The term "heterocyclo", "heterocycle" or "heterocyclic ring," as used herein alone or as part of another group, represents an unsubstituted or substituted stable 5- to 7-membered monocyclic ring system which may be saturated or partially unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. "Substituted heterocyclo (or heterocycle or heterocyclic ring) includes a heterocyclic group which may be substituted with 1 to 4 substituents, such as the substituents included above in the definition of "substituted alkyl" "substituted cycloalkyl" and "substituted aryl". The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolidinyl, pyrazolidinyl, imidazolinyl, oxazolidinyl, isoxazolidinyl, morpholinyl, thiazolidinyl, tetrahydropyranyl, thiamorpholinyl, thiamorpholinyl sulfoxide and thiamorpholinyl sulfone.

The term "optionally substituted" is used herein to signify that a chemical moiety referred to, e.g., alkyl, aryl, heteroaryl, may be unsubstituted or substituted with one or more groups including, without limitation, lower alkyl, alkenyl, alkynyl, cycloalkyl, arylalkyl, aryl, haloaryl, heterocycle, heterocycloalkyl, heteroaryl, hydroxyl, amino, monoalkylamino, dialkylamino, alkoxy, halogen, haloalkoxy, aryloxy, aryloxyalkyl, alkylaryloxy, arylalkoxy, alkoxyaryl, carboxy, carbalkoxy, carboxamido, aminocarbonyl, monoalkylaminocarbonyl, dialkylaminocarbonyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of formulas I-V, above, that may be optionally substituted include lower alkyl, alkenyl, alkynyl, cycloalkyl, arylalkyl, aryl, heterocycle, and heteroaryl. For example, optionally substituted alkyl would comprise both propyl and 2-chloro-propyl. Additionally, "optionally substituted" is also inclusive of embodiments where the named substituent or substituents have multiple substituents rather than simply a single substituent. For example, optionally substituted aryl would comprise both phenyl and 3-bromo-4-chloro-6-ethyl-phenyl.

Unless expressly indicated otherwise, all references herein to alkyl and aryl groups also include the substituted forms thereof.

Among the substituents of the A moiety represented by R1 in Formula I, above, preferred are H or optionally substituted (C1-C3)-alkyl at the 3-position, and where the 4- and 5-positions are joined together to form an optionally substituted 6-membered aromatic ring; and particularly preferred substituents are H or $CH_3$ at the 3-position, and a fused benzene ring at the 4- and 5-positions optionally substituted with halogen and $(C_1-C_3)$-alkoxy.

Among the substituents represented by R3 in Formulas II, III and IV, above preferred are H, halogen, or $(C_1-C_3)$-alkoxy; and particularly preferred are H and (C1-C3) alkoxy.

As used herein, the term "subject" includes both humans and animals. As used herein, the term "PCSK9" refers to any form of the protein PCSK9, including PCSK9 mutants and variants, which retain at least part of PCSK9 activity or function. Unless otherwise indicated, such as by specific reference to human PCSK9, PCSK9 refers to all mammalian species of native sequence PCSK9, e.g., human, porcine, bovine, equine, canine and feline. One exemplary human PCSK9 sequence is found as Uniprot Accession Number Q8NBP7.

As used herein, a "modulator of PCSK9 function" refers to a small molecule that is able to inhibit PCSK9 biological activity or function, and/or downstream pathway(s) mediated by PCSK9 signaling, including PCSK9-mediated down-regulation of the LDLR, and PCSK9-mediated inhibition of the decrease in LDL blood clearance. A modulator of PCSK9 function encompasses compounds that block, antagonize, suppress or reduce (to any degree including significantly) PCSK9 biological activity, including downstream pathways mediated by PCSK9 signaling, such as LDLR interaction and/or elicitation of a cellular response to PCSK9. For purpose of the present invention, it will be explicitly understood that the term "modulator of PCSK9 function" encompasses all the previously identified terms, titles, and functional states and characteristics whereby the PCSK9 itself, a PCSK9 biological activity (including but not limited to its ability to mediate any aspect of interaction with the LDLR, down regulation of LDLR, and inhibit the decrease in blood LDL clearance), or the consequences of the biological activity, are substantially nullified, decreased, or neutralized in any measurable degree. In some embodiments, a modulator of PCSK9 function binds PCSK9 and prevents its interaction with the LDLR or its secretion. In other embodiments, a modulator of PCSK9 function binds to the active site of PCSK9 to stabilize its zymogen and prevent autoprocessing. In further embodiments, a modulator of PCSK9 function decreases or blocks PCSK9 mediated down-regulation of the LDLR; inhibits the PCSK9-mediated decrease in LDL blood clearance; increases LDL clearance in media by cultured hepatocytes; increases blood LDL clearance by the liver in vivo; improves patients' sensitivity to other LDL lowering drugs, including statins; is synergistic to other LDL lowering drugs, including statins; and blocks PCSK9 interaction with other yet to be identified factors. Examples of modulators of PCSK9 function are provided herein.

The compounds used in the method of the invention can be administered as salts, which are also within the scope of this invention. Pharmaceutically acceptable (i.e., non-toxic, physiologically compatible) salts are preferred. If the compounds of the method of the present invention have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid or lysine or arginine, or benzoic acid, or with organic sulfonic acids, such as (C1-C4) alkyl or arylsulfonic acids which are unsubstituted or substituted, for example by halogen, for example methyl- or para-toluene-sulfonic acid. Corresponding acid addition salts can also be formed having plural basic centers, if desired. The compounds used in the method of the present invention having at least one acid group (for example COOH) can also form salts with suitable bases. Representative examples of such salts include metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may also be formed.

Preferred salts of the compounds described herein which contain a basic group include monohydrochloride, hydrogensulfate, methanesulfonate, phosphate or nitrate.

Preferred salts of the compounds described herein which contain an acid group include sodium, potassium and magnesium salts and pharmaceutically acceptable organic amines.

All stereoisomers of the compounds which may be used in the methods described herein, either in a mixture or in pure or substantially pure form, are considered to be within the scope of this invention. The compounds of the present invention can have asymmetric centers at any of the carbon atoms including any one of the R substituents. Consequently, compounds used in the method of the invention can exist in enantiomeric or diastereomeric forms or in mixtures thereof. The processes for preparation of such compounds can utilize racemates, enantiomers or diastereomers as starting materials. When diastereomeric or enantiomeric products are prepared, they can be separated by conventional methods for example, chromatographic, chiral HPLC or fractional crystallization.

As used herein, the term "pharmacophore" refers to the ensemble of steric and electronic features that are necessary to ensure the optimal supramolecular interactions with a specific biological target structure and to trigger, activate, block, inhibit or modulate the biological target's biological activity, as the case may be. See, IUPAC, *Pure and Applied Chemistry* (1998) 70: 1129-1143.

As used herein, the term "pharmacophore model" refers to a representation of points in a defined coordinate system wherein a point corresponds to a position or other characteristic of an atom or chemical moiety in a bound conformation of a ligand and/or an interacting polypeptide, protein, or ordered water molecule. An ordered water molecule is an observable water in a model derived from structural determination of a polypeptide or protein. A pharmacophore model can include, for example, atoms of a bound conformation of a ligand, or portion thereof. A pharmacophore model can include both the bound conformations of a ligand, or portion thereof, and one or more atoms that interact with the ligand and are from a bound polypeptide or protein. Thus, in addition to geometric characteristics of a bound conformation of a ligand, a pharmacophore model can indicate other characteristics including, for example, charge or hydrophobicity of an atom or chemical moiety. A pharmacophore model can incorporate internal interactions within the bound conformation of a ligand or interactions between a bound conformation of a ligand and a polypeptide, protein, or other receptor including, for example, van der Waals interactions, hydrogen bonds, ionic bonds, and hydrophobic interactions. A pharmacophore model can be derived from two or more bound conformations of a ligand.

As used herein, the term "ligand" refers to any compound, composition or molecule that interacts with the ligand binding domain of a receptor and modulates its activity. A "ligand" may also include compounds that modulate the receptor without binding directly to it.

In carrying out the method of the invention, the above-described compounds may be administered as such, or in a form from which the active agent can be derived, such as a prodrug. A prodrug is a derivative of a compound described herein, the pharmacologic action of which results from the conversion by chemical or metabolic processes in vivo to the active compound. The term "prodrug esters" as employed herein includes esters and carbonates formed by reacting one or more hydroxyls of compounds used in the method of the invention with alkyl, alkoxy, or aryl substituted acylating agents employing procedures known to those skilled in the art to generate acetates, pivalates, methylcarbonates, benzoates and the like. Any compound that can be converted in vivo to provide the bioactive agent (i.e., a compound of formula I) is a prodrug within the scope and spirit of the invention. Various forms of prodrugs are well known in the art. A comprehensive description of prodrugs and prodrug derivatives are described in: (a) The Practice of Medicinal Chemistry, Camille G. Wermuth et al., Ch 31 (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., Ch. 5, pgs, 113-191 (Harwood Academic Publishers, 1991).

The therapeutic agent used in practicing the method of the invention is administered in an amount sufficient to induce the desired therapeutic effect in the recipient thereof. Thus the term "therapeutically effective amount" as used herein refers to an amount of a therapeutic agent which is sufficient to treat or prevent a condition treatable by administration of one or more of the compounds of formulas I-V or a prodrug thereof. Preferably, the therapeutically effective amount refers to the amount appropriate to treat a PCSK9-associated condition, i.e. to bring almost a detectable therapeutic or preventative or ameliorative effect. The effect may include, for example, treatment or prevention of the conditions described herein.

The compound(s) described herein may be administered at a dose in range from about 0.01 mg to about 200 mg/kg of body weight per day. A dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds used in the method of the invention will typically be administered from 1-4 times a day, so as to deliver the above-mentioned daily dosage. However, the exact regimen for administration of the compounds described herein will necessarily be dependent on the needs of the individual subject being treated, the type of treatment administered and the judgment of the attending medical specialist.

In one aspect, the invention provides a method for treating or preventing hypercholesterolemia, and/or at least one symptom of dyslipidemia, atherosclerosis, CVD or coronary heart disease, in an individual comprising administering to the individual an effective amount of a modulator of PCSK9 function that antagonizes circulating PCSK9.

In a further aspect, the invention provides an effective amount of a modulator of PCSK9 function that antagonizes circulating PCSK9 for use in treating or preventing hypercholesterolemia, and/or at least one symptom of dyslipidemia, atherosclerosis, CVD or coronary heart disease, in an individual. The invention further provides the use of an effective amount of a modulator of PCSK9 function that antagonizes extracellular or circulating PCSK9 in the manufacture of a medicament for treating or preventing hypercholesterolemia, and/or at least one symptom of dyslipidemia, atherosclerosis, CVD or coronary heart disease, in an individual.

The methods of the invention use a modulator of PCSK9 function, which refers to any molecule that blocks, suppresses or reduces (including significantly reduces) PCSK9 biological activity, including downstream pathways mediated by PCSK9 signaling, such as elicitation of a cellular response to PCSK9.

A modulator of PCSK9 function should exhibit any one or more of the following characteristics: (a) bind to PCSK9; (b) decrease or block PCSK9 interaction with the LDLR; (c) decrease or block secretion of PCSK9; (d) decrease or block PCSK9 mediated down-regulation of the LDLR; (e) inhibit the PCSK9-mediated decrease in LDL blood clearance, (f) increase LDL clearance in media by cultured hepatocytes, (g) increase blood LDL clearance by the liver in vivo, (h) improve patients' sensitivity to other LDL lowering drugs, including statins, (i) is synergistic to other LDL lowering drugs, including statins; and (j) block PCSK9 interaction with other yet to be identified factors.

In general, the compound(s) used in the method of the invention can be administered to achieve modulation of PCSK9 function by using any acceptable route known in the art, either alone or in combination with one or more other therapeutic agents. Thus, the active agent(s) can be administered orally, buccally, parenterally, such as by intravenous or intra-arterial infusion, intramuscular, intraperitoneal, intrathecal or subcutaneous injection, by liposome-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agent may also be incorporated into a conventional transdermal delivery system.

As used herein, the expression "physiologically compatible carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20$^{th}$ edition (A. R. Genaro et al., Part 5, Pharmaceutical Manufacturing, pp. 669-1015 (Lippincott Williams & Wilkins, Baltimore, Md./Philadelphia, Pa.) (2000)) discloses various carriers used in formulating pharmaceutical compositions and known techniques for the preparation thereof. Except insofar as any conventional pharmaceutical carrier medium is incompatible with the PCSK9 modulators used in the present invention, such as by producing an undesirable biological effect or otherwise interacting in an deleterious manner with any other component(s) of a formulation comprising such compounds, its use is contemplated to be within the scope of this invention.

For the production of solid dosage forms, including hard and soft capsules, the therapeutic agent may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further includes controlled-release, sustained-release, or extended-release therapeutic dosage forms for administration of the active agent, which involves incorporation of the active agent into a suitable delivery system. This dosage form controls release of the active agent(s) in such a manner that an effective concentration of the active agent(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

In pharmaceutical compositions used in practicing the method of the invention, the active agent(s) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

Compounds for use in practicing this invention include those of formulas I-IV, above. More preferred are the compounds set out in FIG. 2. Most preferred are the compounds set out in FIG. 3.

Some of the compounds described herein are obtainable from commercial sources, such as Life Chemicals (SBC-115,202), Enamine (SBC-115,270 and SBC-115,271), ChemBridge (SBC-115,337), and Princeton Biomolecular (SBC-115,341). Other preferred compounds and almost all of the most preferred compounds were not available from commercial sources but were synthesized using methods known to those skilled in the art of organic synthesis.

The methods of the present invention will normally include medical follow-up to determine the therapeutic or prophylactic effect brought about in the subject undergoing treatment with the compound(s) and/or composition(s) described herein.

The activities of compounds described herein have been experimentally demonstrated. The following examples are provided to describe the invention in further detail. These examples are provided for illustrative purposes only and are not intended to limit the invention in any way.

EXAMPLE 1

Test for LDLR/PCSK9 Binding

Figure 2:
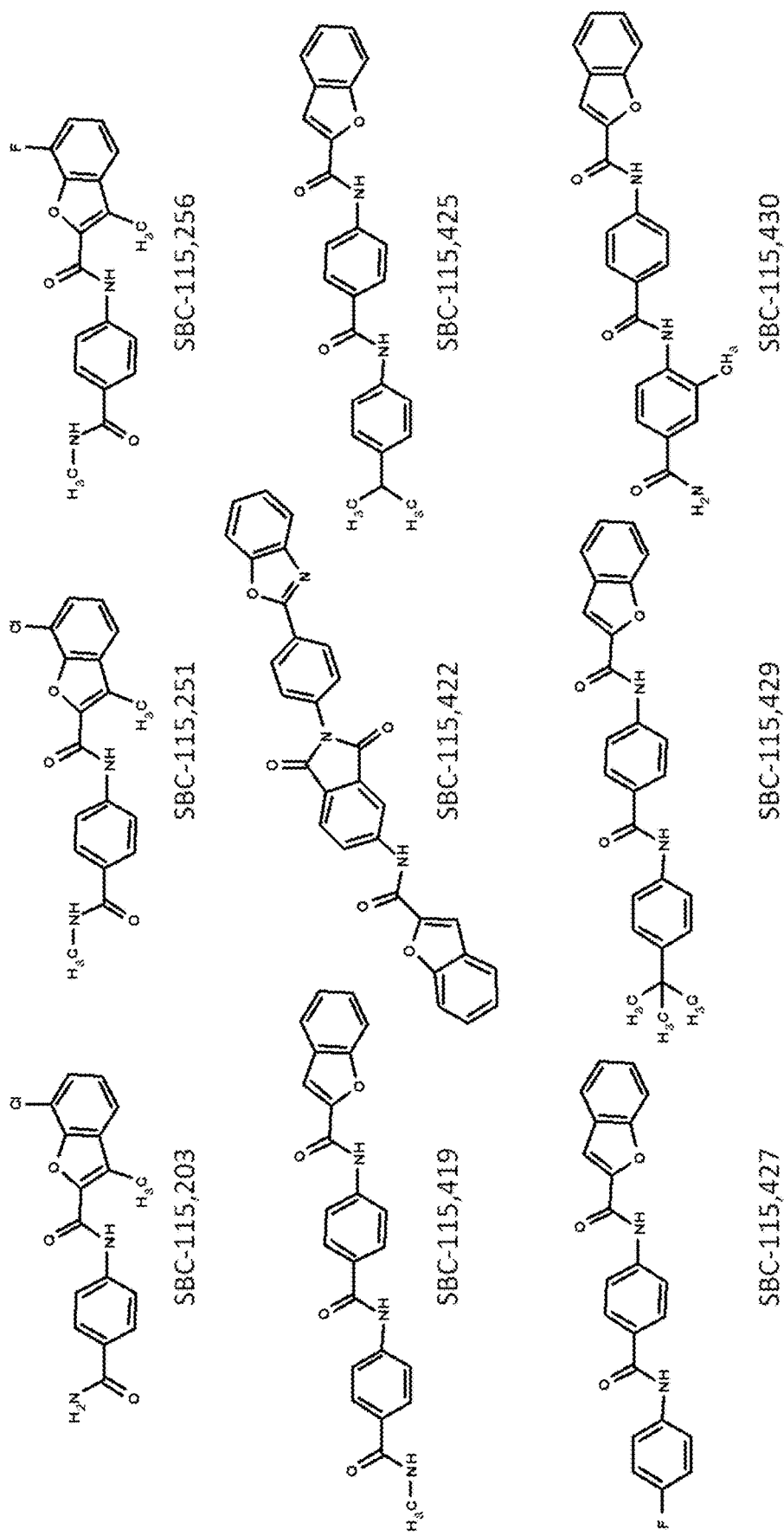
Figure 2:
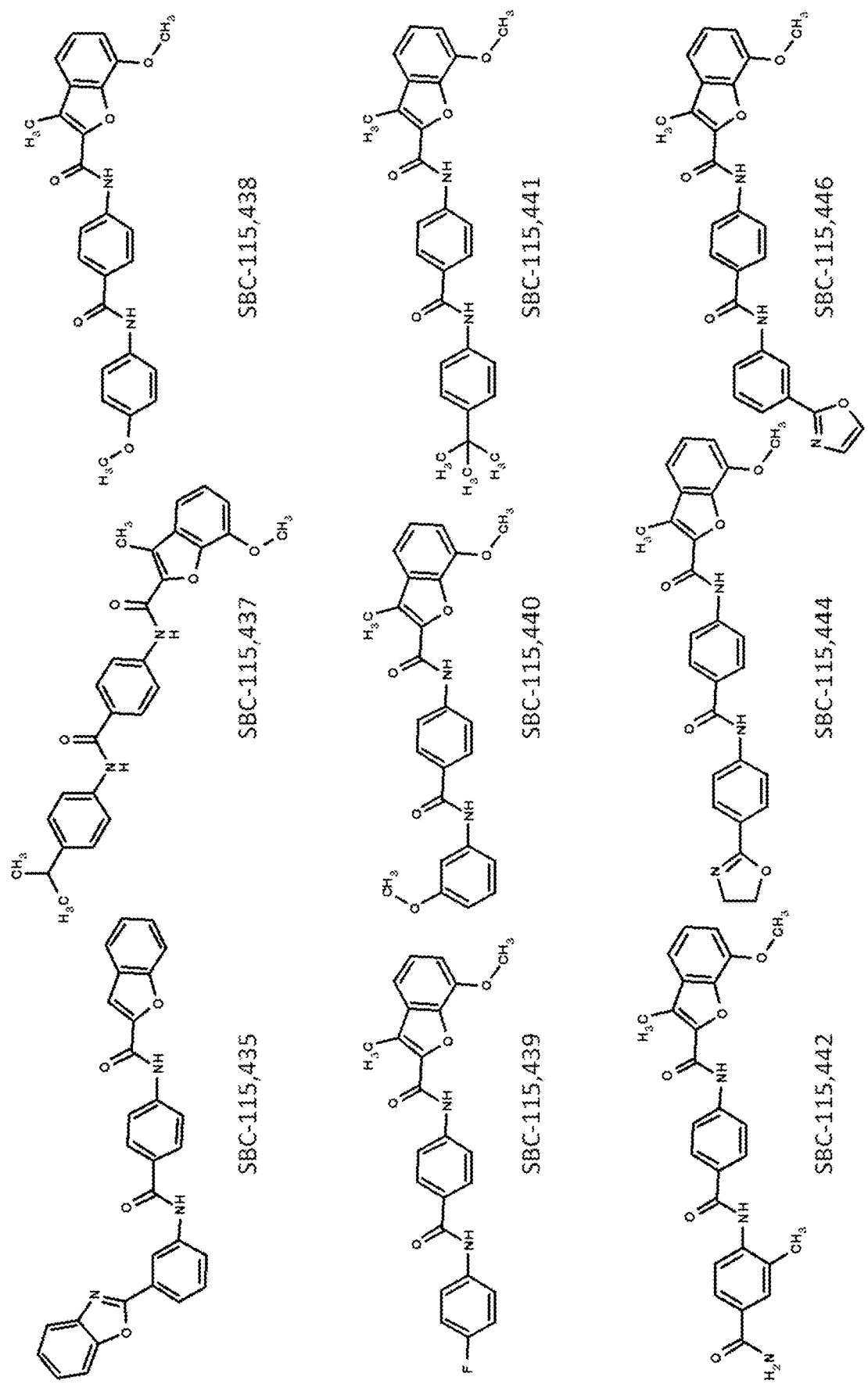
Figure 3:
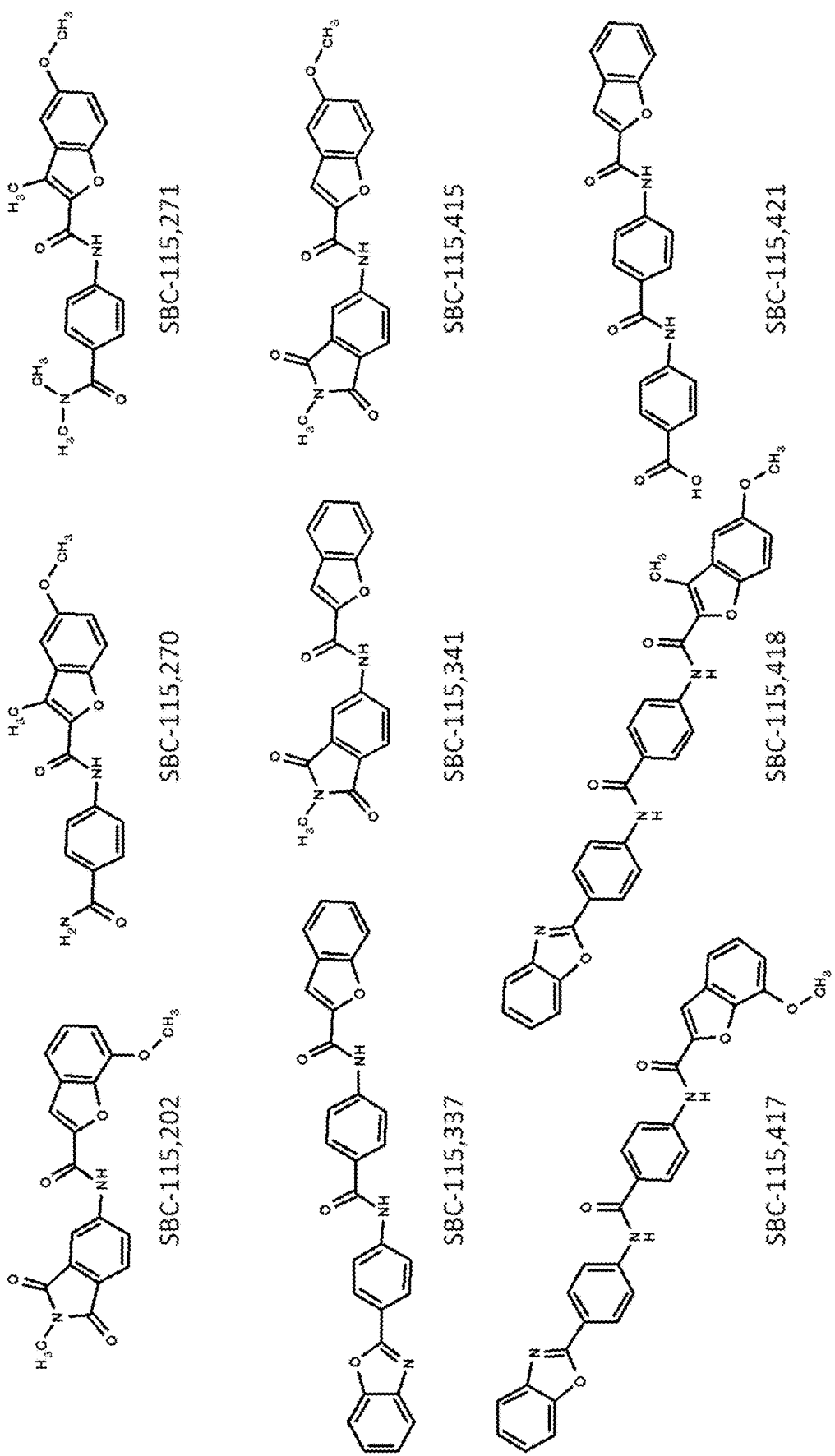
Figure 3:
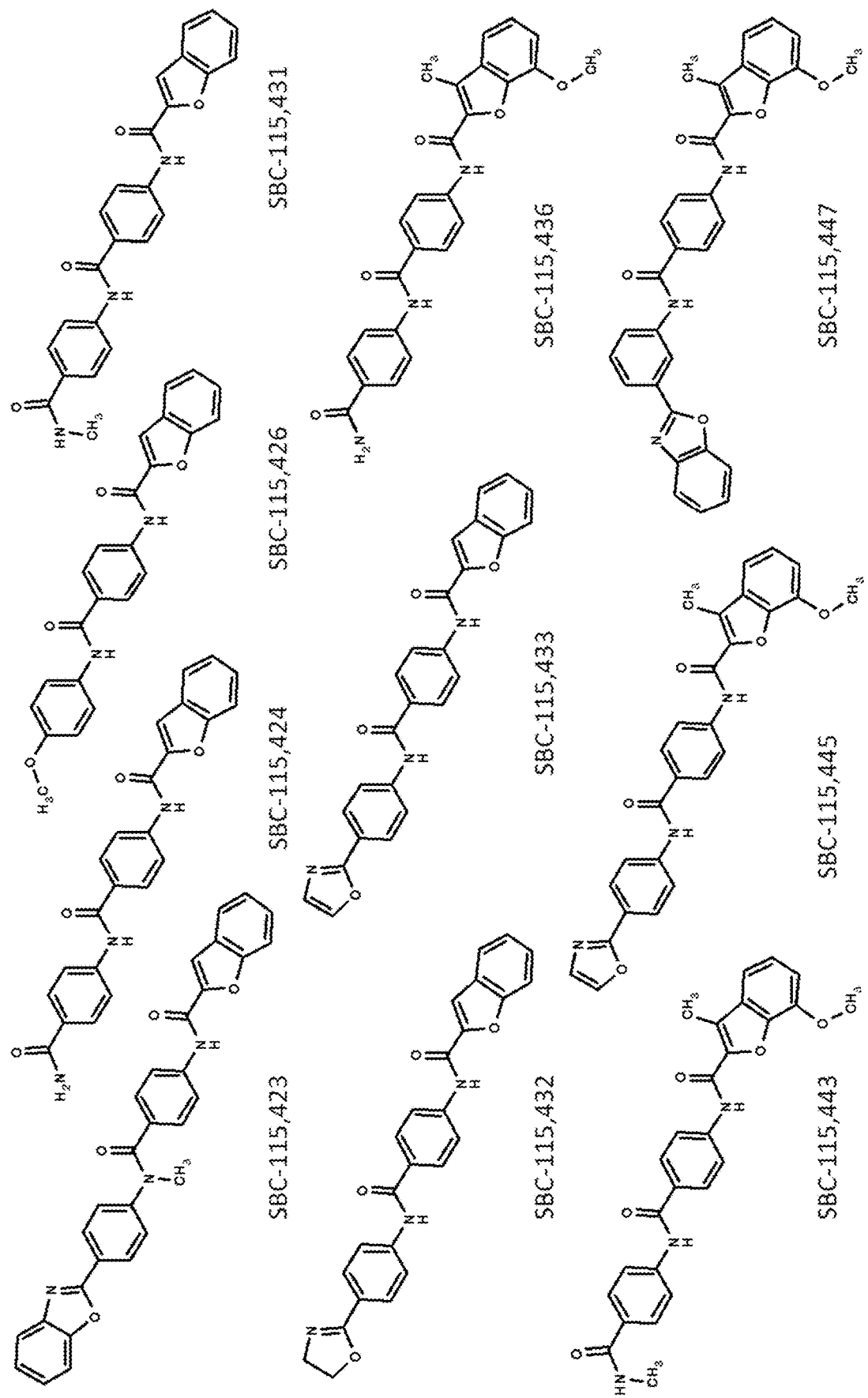
Figure 4:
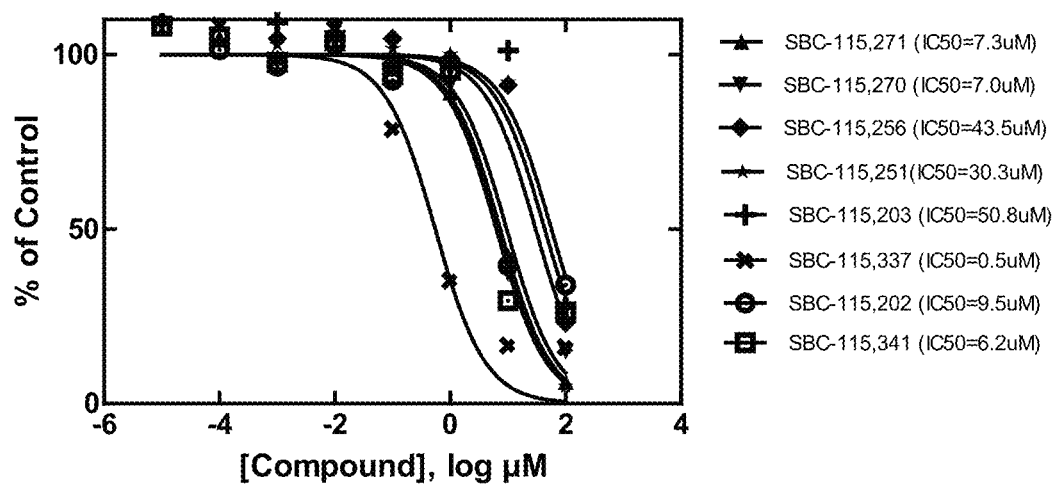
Figure 11:
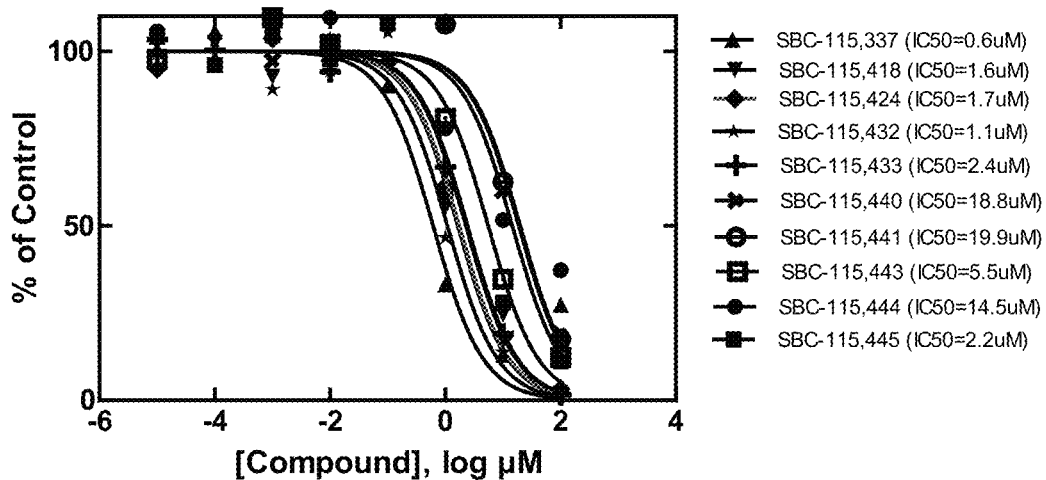
FIG. 11 shows the SAR around SBC-115,337 on the PCSK9/LDLR interaction: an in vitro ELISA assay kit was utilized as described in FIG. 4.

Testing of compounds acquired from commercial sources was performed in our binding assay for their potential to inhibit the PCSK9/LDLR interaction. Initial screening was done using 100 µM of the compounds. Each compound was added to the binding reaction mixture in triplicate and assayed as described above. From the screening, a number of compounds were identified to have an effect on LDLR upregulation as compared to control (see Example 3 vide infra) while having no effect on PCSK9 processing and secretion (see Example 2 vide infra). Exemplary 2-carboxyanilide indoles and 2-carboxanilide pyrroles of the formula I that had >20% inhibition at 100 uM are shown in FIG. 1. Fifty five (55) structurally related 2-carboxyanlide benzofurans (compounds of the formulas II-IV) were also acquired. Compounds that inhibited the PCSK9/LDLR interaction were selected and analyzed using different compound concentrations ranging from 100 µM to 0.01 nM. The most potent benzofuran compounds were SBC-115,270, SBC-115,271, SBC-115,337 and SBC-115,202 with IC50's of 7, 7.3, 0.5 and 9.5 µM, resp. (FIG. 4). Based on this preliminary SAR, an additional 34 compounds were designed and synthesized around SBC-115,337, and the compounds were tested in our binding assay as described in FIG. 4. From the screening, a number of benzofuran compounds were determined to have IC50's>10 uM but less </=50 uM (FIG. 2). Still more potent compounds had IC50's<10 uM (FIG. 3). FIG. 11 and Table 1 shows the IC50's of the best ten of these compounds. Compounds that exhibited low or submicromolar potency were selected for further evaluation in multiple different cell based assays.

TABLE 1

Summary of the IC50 of SBC-115,337 and eleven analogs

| Compound | IC-50 (µM) |
| --- | --- |
| SBC-115,337 | 0.6 |
| SBC-115,415 | 5.9 |
| SBC-115,418 | 1.6 |
| SBC-115,423 | 8.2 |
| SBC-115,424 | 1.7 |
| SBC-115,432 | 1.1 |
| SBC-115,433 | 2.4 |
| SBC-115,440 | 18.8 |
| SBC-115,441 | 19.9 |
| SBC-115,443 | 5.5 |
| SBC-115,444 | 14.5 |
| SBC-115,445 | 2.2 |

EXAMPLE 2

Test for Secreted PCSK9

Figure 5:
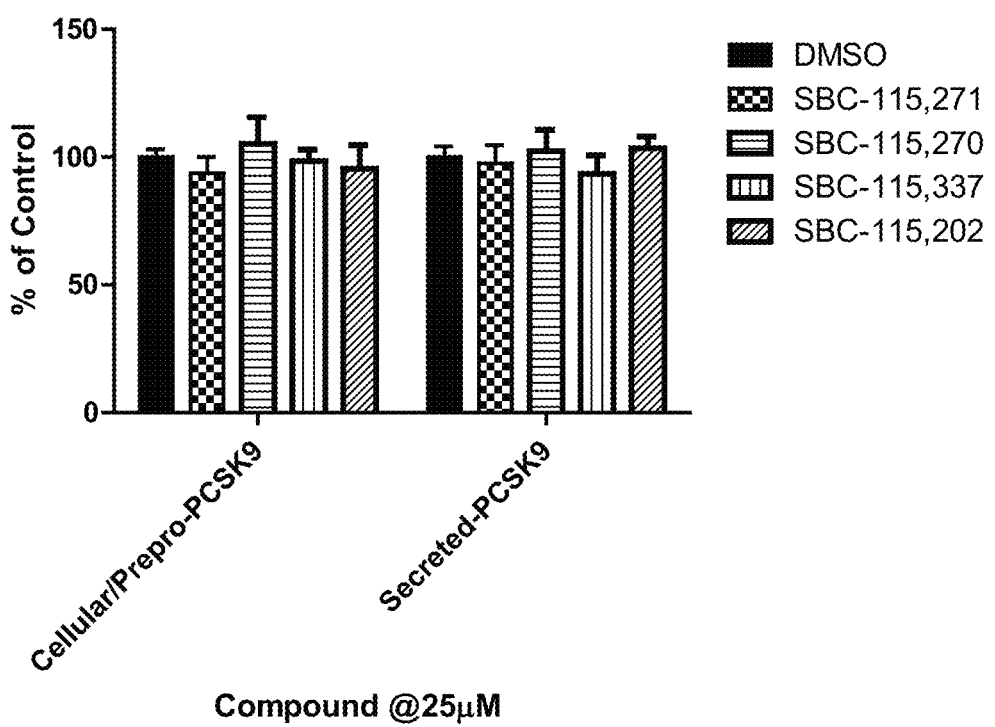

The increase in the level of recombinant LDLR in the presence of PCSK9 by the above compounds could be either due to inhibiting the binding of PCSK9 to the LDLR or by inhibiting the processing and secretion of PCSK9. To eliminate the possibility these compounds interfere with PCSK9 synthesis, processing or secretion, we tested the effect of these compounds on the processing and secretion of PCSK9 as described above. HEK-293T cells were seeded into 96-well plates in a DMEM containing 10% Fetal Bovine Serum media and incubated overnight at 37° C. Cells were transiently transfected with cDNA construct using the Lipofectamine-LTX. Compounds (25 µM) or vehicle were added, followed by additional 43 hours of incubation. Cellular PCSK9, secreted PCSK9, and cell viability were analyzed for PCSK9 secretion using western blot analysis, imaged and quantitated using a LAS-4000 (GE). Results from four selected compounds are shown in FIG. 5. All of these compounds exhibited no effect on the synthesis, processing and secretion of PCSK9 either in the cells or into the media (FIG. 5).

EXAMPLE 3

Test for LDLR Upregulation

Figure 6:
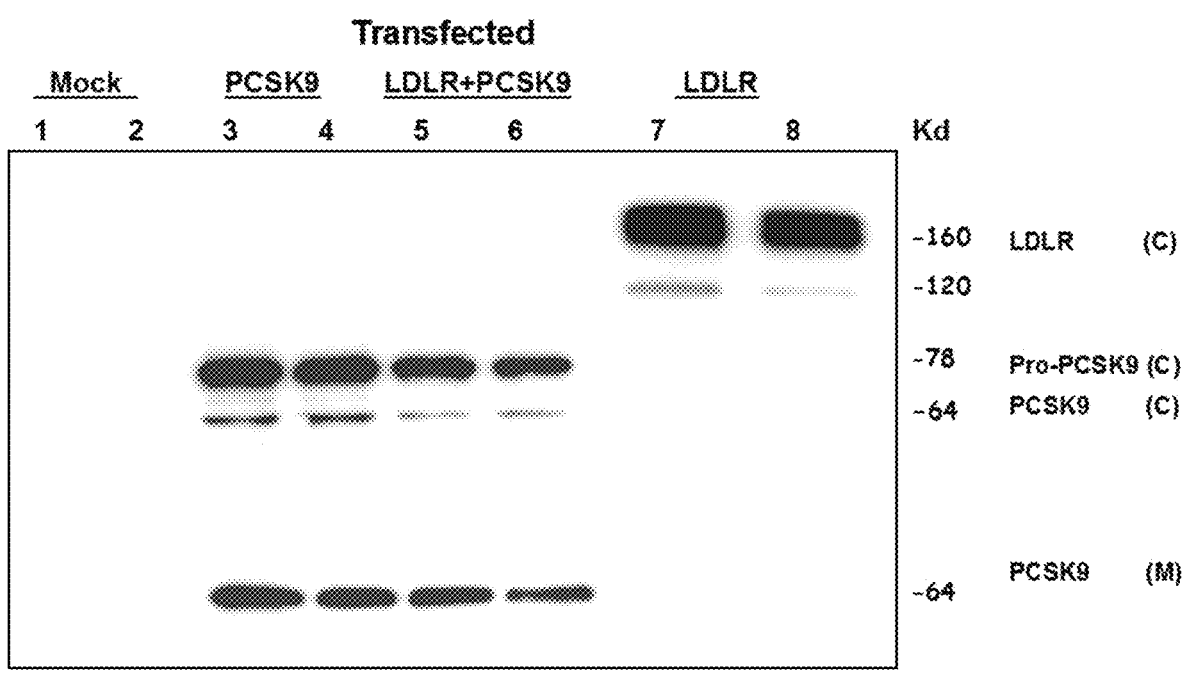
Figure 7:
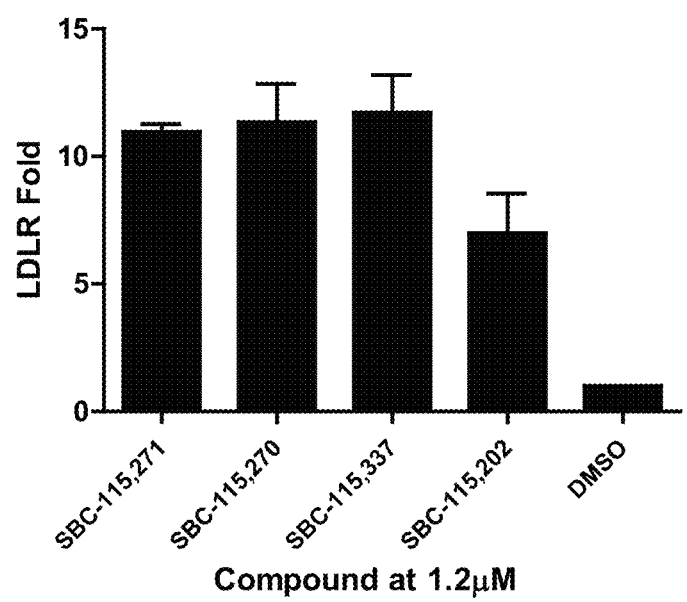

We used our own recombinant assay which demonstrates that co-expression of PCSK9 and LDLR DNA in HEK-293 cells results in a decrease in the expression level of intracellular LDLRs. We have constructed the expression vector of human LDLR under the control of the cytomegalovirus promoter-enhancer (pCMV-LDLR). In addition, a construct containing the PCSK9 (pCMV-PCSK9-FLAG) was described above. These constructs were used to transiently transfect mammalian cells, and both cell lysate and supernatant were subjected to SDS-PAGE and immunoblot analysis using an anti-PCSK9 or LDLR antibody. The data from the blot showed that cells that were transfected with only pCMV-PCSK9-FLAG expressed both the unprocessed (cells) and processed (media) PCSK9 (FIG. 6). Cells that were transfected with only pCMV-LDLR showed expression of the LDLR in the cells (FIG. 6). However, cells that were transfected with both pCMV-PCSK9-FLAG and pCMV-LDLR showed disappearance of the intracellular LDLR band (FIG. 6), which provides further evidence that the presence of PCSK9 results in degradation of LDLR or chaperones it to the degradation pathway. Addition of inhibitors of PCSK9 processing to the latter cells should result in decreased degradation of the LDLR and the appearance of the 160K Dalton band on the gel. Using this assay, we tested our compounds for their ability to reduce the degradation of the LDLR. HEK-293 cells were used in this assay. They were grown in 96-well plates overnight, and transfected with LDLR/PCSK9. Compounds dissolved in DMSO or vehicle were added to the culture media, and incubated for 24-48 hours; cells were lysed. Cell lysates were subjected to quantitation using the above immunoassay. FIG. 7 shows the effect of four compounds on the intracellular recombinant LDLR upregulation. Compounds SBC-115,270, SBC-115,271, SBC-115,337 and SBC-115,202 exhibited a 5 to 10 fold up-regulation at 1.2 µM.

Figure 8:
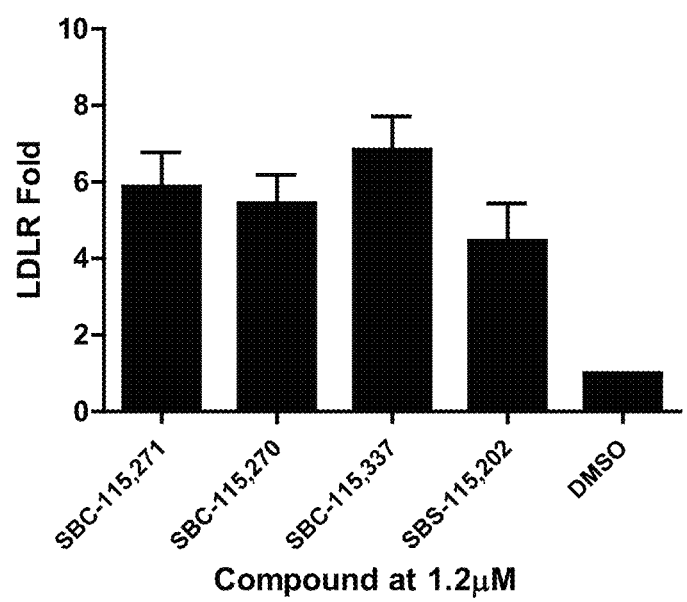

Testing confirmed that these compounds are capable of upregulating the endogenously expressed LDLR in HepG2 cells. HepG2 cells transfected with PCSK9 were cultured in 96-well plates at a density of 30,000 cells per well. The next day, cells are treated with selected screening compounds or vehicle. Cells were incubated for 48 hrs and then subjected to quantitation using an LDL receptor-polyclonal antibody and analyzed as described above. The data in FIG. 8 shows that these compounds exhibited an increase in the level of LDLR as compared to cells treated with the same volume of DMSO with a 4-8 fold upregulation of LDLR.

EXAMPLE 4

Uptake of Dil-LDL in HepG2 Cells In Situ

Figure 9:
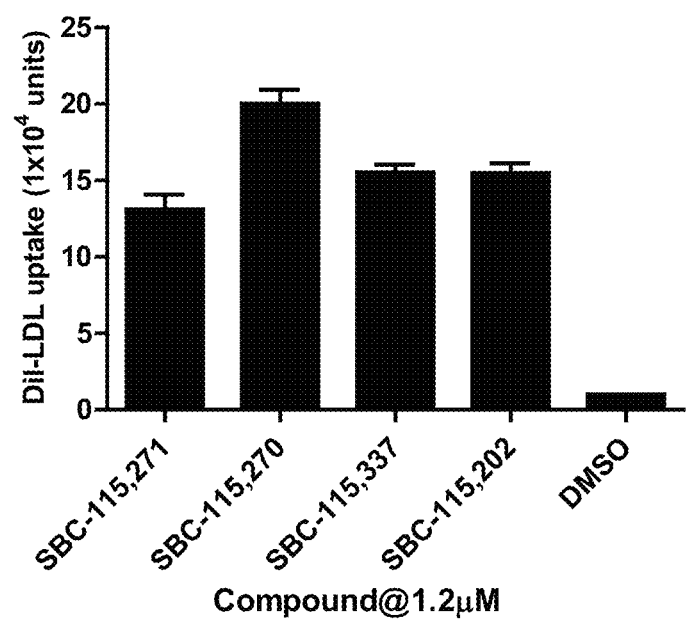
Figure 12:
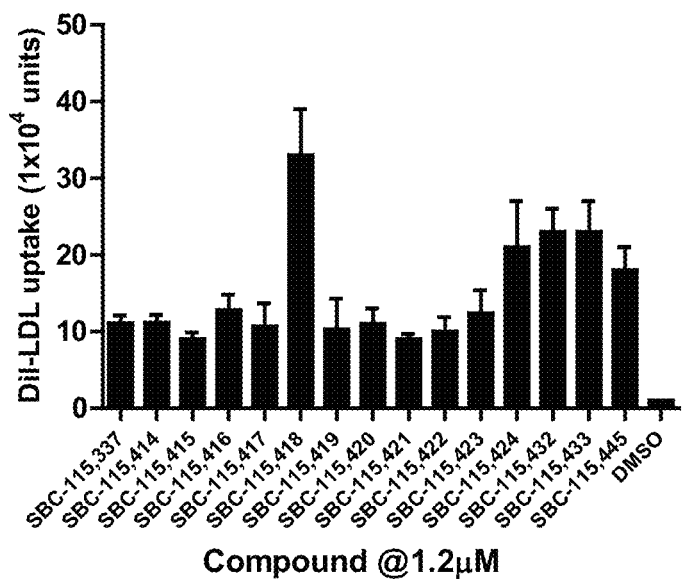
FIG. 12 shows increased uptake of Fluorescent Dil-LDL using various inhibitors in HepG2 cells. The SBC compounds were validated for their ability to increase uptake of Fluorescent Dil-LDL in HepG2 cells as described in FIG. 9.

In order to confirm that these PCSK9 antagonists upregulate functional LDLR, we tested the ability of these compounds to enhance the uptake of fluorescent Dil-LDL in HepG2 cells. Briefly, HepG2 cells transfected with PCSK9 (FIG. 4) were plated and allowed to grow overnight. Compounds were added to the cells followed by the addition of fluorescent Dil-LDL. Cells were washed extensively, and the fluorescent Dil-LDL taken up by the cells were measured using the Synergy 2 plate reader (FIG. 9 and FIG. 12). As shown in FIG. 9, our compounds (SBC-115,337, SBC-115,270, SBC-115,271 and SBC-115,202) exhibited an increase in fluorescently labeled LDL uptake in HepG2 treated cells at 1.2 uM. Further analysis of additional selected compounds from our binding studies (Table 1) showed that four compounds (SBC-115,418, SBC-115,424, SBC-115,432 and SBC-115,433) exhibited significant increases in the Dil-LDL uptake at 1.2 uM compound concentration (FIG. 12). These compounds were selected for further analysis in the in vivo studies.

EXAMPLE 5

Test for LDLR Upregulation

Figure 13:
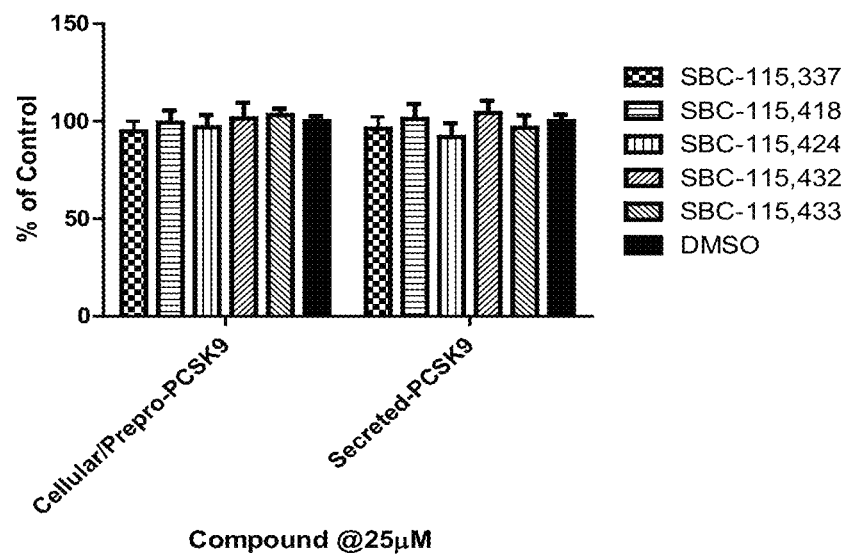
FIG. 13 shows the effect of different compounds on PCSK9 synthesis, processing and secretion in HEK293/PCSK9 transfected cells. The SBC compounds were validated for their ability to affect PCSK9 synthesis, processing and secretion as described in relation to FIG. 5.

We used our recombinant LDLR upregulation assay (Example 3) to validate that SBC-115,418, SBC-115,424, SBC-115,432 and SBC-115,433 exhibited a significant increase in the level of LDLR as compared to cells treated with the same volume of DMSO (FIG. 13).

EXAMPLE 6

Test for Secreted PCSK9

Figure 14:
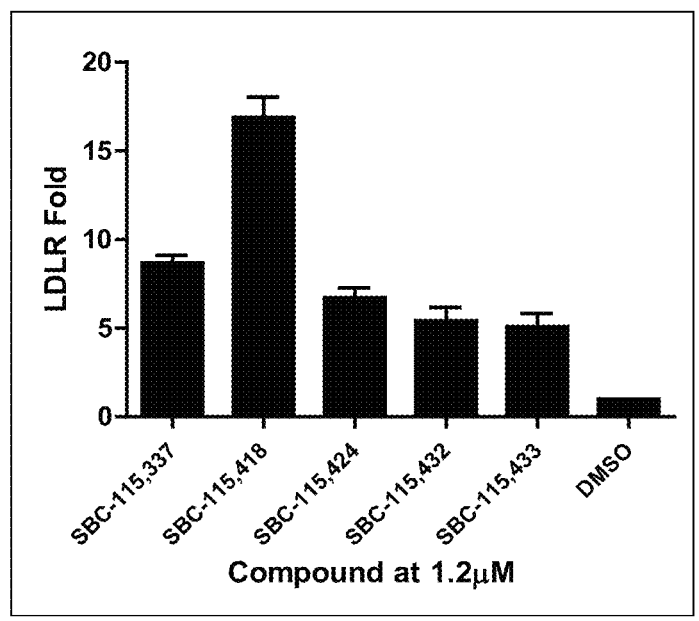
FIG. 14 shows the upregulation of LDLR by PCSK9 antagonists. HEK-293T cells were assayed as described in relation to FIG. 7.

The increase in the level of recombinant LDLR of the four selected compounds (SBC-115,418, SBC-115,424, SBC-115,432 and SBC-115,433) shown in FIG. 14 is not due to its effect on synthesis and secretion of PCSK9, but rather on its effect on the LDLR/PCSK9 interaction (see example 2).

EXAMPLE 7

Test for Cell Viability

All compounds that upregulate the endogenously expressed LDLR were used to test for in situ cell viability. HEK-293T cells or HepG2 cells were seeded in 96-well plates in a cell media containing 10% Fetal Bovine Serum and incubated overnight at 37° C. Compounds (25 uM) were added to cells after 24 hours and incubated for an additional 48 hours. Cell viability was assayed using Resazurin (Sigma 199303) and a Synergy-II plate reader. Compounds that showed cell toxicity were excluded.

EXAMPLE 8

Test for Efficacy in an Animal Model

Figure 10:
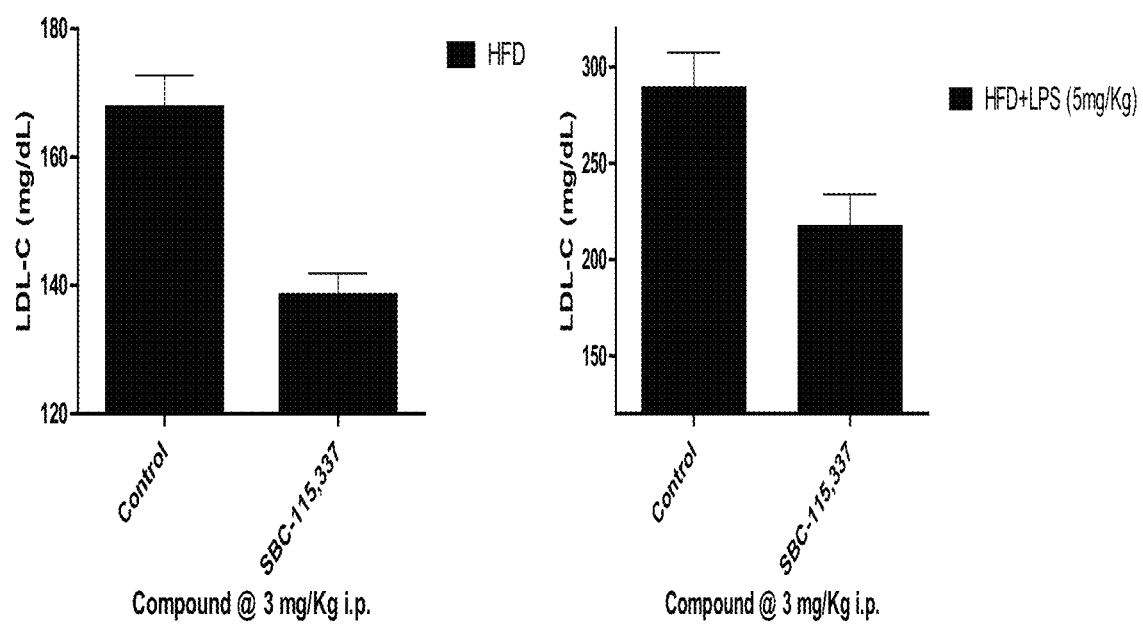

SBC-115,337 was tested for efficacy in male mice ($C_{57}BL/6$ mice). Mice were housed as four animals per cage under climate-controlled conditions of temperature (20-24° C.), humidity (60-70%), and alternating 12 h light/dark cycles. The mice were divided into five groups as shown in FIG. 10. One group was fed commercial chow diet (Prolab RMH 3000, PMI feeds, St. Louis, Mo.) to serve as a negative control, while the other four groups were fed high fat diet (TD.06414), which provides 60% of calories from fat. Water was provided ad libitum. Plasma was collected once weekly to monitor the level of LDL. After 4 weeks of feeding a high fat-diet, mice were randomly assigned to one of several groups such that the average LDL levels were equal among different groups. One of the four groups of mice fed high fat diet was treated with vehicle and served as a positive control, whereas the second group was treated daily with 3 mg/kg of SBC-115,337 subcutaneously for 4 days. The third group of mice fed high fat diet was treated with vehicle and LPS (5 mg/Kg) and served as a LPS positive control, whereas the fourth group was treated daily with 3 mg/kg SBC-115,337+LPS (5 mg/Kg) subcutaneously for 4 days.

Blood samples (75 µl) were collected 4 days after drug administration from the retro-orbital venous plexus via heparinized capillary tubes containing 2 USP units of ammonium heparin per tube (Carolina, Burlington, N.C.). Plasma was separated immediately by centrifugation (5,000×g) for 5 min at room temperature and then kept at −80° C. until assayed for lipid profile. Plasma cholesterol, LDL-C, HDL-C, and triglyceride levels were measured enzymatically.

Our data demonstrated that SBC-115,337 lowered LDL-C levels in mice that are fed high fat diet and treated or untreated with LPS. FIG. 10 shows data obtained with SBC-115,337 indicating a 20-25% reduction in LDL-C levels after 4 days relative to high fat diet animal levels.

Figure 15A:
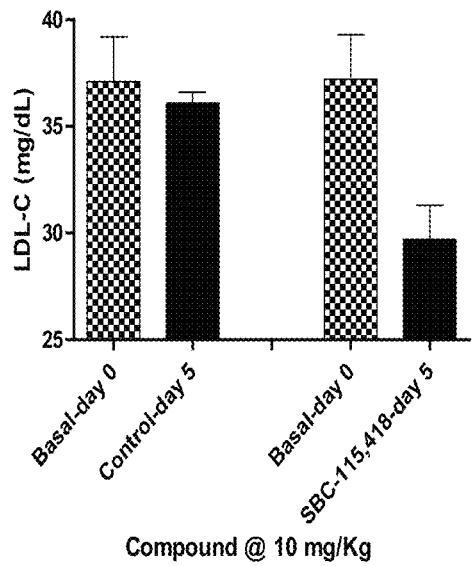
FIG. 15A-FIG. 15B shows the effect of SBC-115,418 on LDL cholesterol levels in C57/Black6 mice fed high fat diet.
Figure 15B:
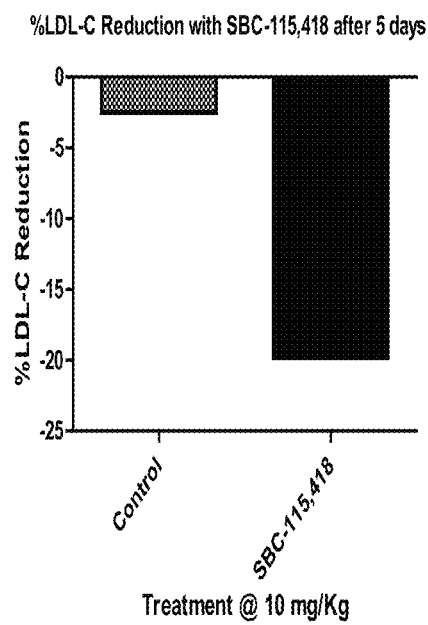

Similarly, SBC-115,418 was tested in mice as described above. C57BL/6 mice were divided into 4 groups of 5 animals in each; two base line groups, a control group that received PBS and a SBC-group that received 10 mg/kg oral daily for 5 days. Blood plasma was collected at day 1 prior to injection of the compounds. Blood plasma was collected again at day 5. Plasma LDL-C levels were measured enzymatically. (A) Representing the actual change in the LDL-C in mg/dL and (B) representing the % reduction of LDL-C after the administration of SBC-115,418 for 5 days. Our data demonstrated that SBC-115,418 lowered LDL-C levels in mice that are fed high fat diet. FIG. 15A and FIG. 15B shows data obtained with SBC-115,418 indicating a 20-25% reduction in LDL-C levels after 5 days of daily oral administration of 10 mg/kg of SBC-115,418 relative to high fat diet animal levels.

The foregoing specification includes citations to certain publications, which are provided to indicate the state of the art to which this invention pertains. The entire disclosure of each of the cited publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All compositions and methods of use thereof that embody the present invention can, in alternate embodiments, be more specifically defined by any of the transitional terms "comprising," "consisting essentially of," and "consisting of."

REFERENCES

1. Grundy S M, Cleeman J I, Merz C N B, Brewer, Jr, H B, Clark L T, Hunninghake D B, Pasternak R C, Smith, Jr, S C, Stone N J (2004). Implications of Recent Clinical Trials for the National Cholesterol Education Program Adult Treatment Panel III Guidelines. *Circulation* 110, 227-239.
2. Abifadel M, Varret M, Rabès J, Allard D, Ouguerram K, Devillers M, Cruaud C, Benjannet S, Wickham L, Erlich D, Derré A, Villéger L, Farnier M, Beucler I, Bruckert E, Chambaz J, Chanu B, Lecerf J, Luc G, Moulin P, Weissenbach J, Prat A, Krempf M, Junien C, Seidah N, Boileau C (2003). Mutations in PCSK9 cause autosomal dominant hypercholesterolemia. *Nat. Genet* 34, 154-156.
3. Pisciotta L, Priore Oliva C, Cefalu A B, Noto D, Bellocchio A, Fresa R, Cantafora A, Patel D, Averna M, Tarugi P, Calandra S, Bertolini S (2006). Additive effect of mutations in LDLR and PCSK9 genes on the phenotype of familial hypercholesterolemia. *Atherosclerosis* 186, 433-440.
4. Maxwell K, Breslow J (2004). Adenoviral-mediated expression of PCSK9 in mice results in a low-density lipoprotein receptor knockout phenotype. *Proc Natl Acad Sci USA* 101, 7100-7105.
5. Benjannet S, Rhainds D, Essalmani R, Mayne J, Wickham L, Jin W, Asselin M, Hamelin J, Varret M, Allard D, Trillard M, Abifadel M, Tebon A, Attie A D, Rader D J, Boileau C, Brissette L, Chrétien M, Prat A, Seidah N G (2004). NARC-1/PCSK9 and its natural mutants: zymogen cleavage and effects on the low density lipoprotein (LDL) receptor and LDL cholesterol. *J Biol Chem* 279, 48865-48875.
6. Cohen J, Pertsemlidis A, Kotowski I, Graham R, Garcia C, Hobbs H (2005). Low LDL cholesterol in individuals of African descent resulting from frequent nonsense mutations in PCSK9. *Nature Genetics* 37, 161-165.
7. Rashid S, Curtis D, Garuti R, Anderson N, Bashmakov Y, Ho Y, Hammer H, Moon Y, Horton J (2005). Decreased plasma cholesterol and hypersensitivity to statins in mice lacking PCSK9. *Proc Natl Acad Sci USA* 102, 5374-5379.
8. Zhao Z, Tuakli-Wosornu Y, Lagace T, Kinch L, Grishin N, Horton J, Cohen J, Hobbs H (2006). Molecular Characterization of Loss-of-Function Mutations in PCSK9 and Identification of a Compound Heterozygote. *Am J Human Genetics* 79, 514-523.
9. Benjannet S, Rhainds D, Hamelin J, Nassoury N, Seidah N G (2006). The proprotein convertase PCSK9 is inactivated by furin and/or PC5/6A: functional consequences of natural mutations and post-translational modifications. *J Biol Chem* 281, 30561-30572.
10. Li J, Tumanut C, Gavigan J-A, Huang W-J, Hampton E N, Tumanut R, Suen K F, Trauger J W, Spraggon G, Lesley S A, Liau G, Yowe D, Harris J L (2007). Secreted PCSK9 promotes LDL receptor degradation independently of proteolytic activity. *Biochem J* 406, 203-207.
11. McNutt M C, Lagace T A, Horton J D (2007). Catalytic activity is not required for secreted PCSK9 to reduce low density lipoprotein receptors in HepG2 cells. *J Biol Chem* 282, 20799-20803.
12. Zhang D-W, Lagace T A, Garuti R, Zhao Z, McDonald M, Horton J D, Cohen J C, Hobbs H H (2007). Binding of proprotein convertase subtilisin/kexin type 9 to epidermal growth factor-like repeat A of low density lipoprotein receptor decreases receptor recycling and increases degradation. *J Biol Chem* 282, 18602-18612.
13. Kwon H J, Lagace T A, McNutt M C, Jay D. Horton J D, Deisenhofer J (2008). Molecular basis for LDL receptor recognition by PCSK9. *Proc Natl Acad Sci USA* 105, 1820-5.

14. Bottomley M J, Cirillo A, Orsatti L, Ruggeri L, Fisher T S, Santoro J C, Cummings R T, Cubbon R M, Lo Surdo P, Calzetta A, Noto A, Baysarowich J, Mattu M, Talamo F, De Francesco R, Sparrow C P, Sitlani A, Carfi A (2009). Structural and biochemical characterization of the wild type PCSK9/EGF(A B) complex and natural familial hypercholesterolemia mutants. *J Biol Chem* 284, 1313-1323.
15. Seidah N G (2009). PCSK9 as a therapeutic target of dyslipidemia. *Expert Opin Ther Targets* 13, 19-28.
16. Graham M J, Lemonidis K M, Whipple C P, Subramaniam A, Monia B P, Crooke S T, Crooke R M (2007). Antisense inhibition of proprotein convertase subtilisin/kexin type 9 reduces serum LDL in hyperlipidemic mice. *J Lipid Res* 48, 763-767.
17. Frank-Kamenetsky M, Grefhorst A, Anderson N N, Racie T S, Bramlage B, Akinc A, Butler D, Charisse K, Dorkin R, Fan Y, Gamba-Vitalo C, Hadwiger P, Jayaraman M, John M, Jayaprakash K N, Maier M, Nechev L, Rajeev K G, Read T, Röhl I, Soutschek J, Tan P, Wong J, Wang G, Zimmermann T, de Fougerolles A, Vornlocher H P, Langer R, Anderson D G, Manoharan M, Koteliansky V, Horton J D, Fitzgerald K (2008). Therapeutic RNAi targeting PCSK9 acutely lowers plasma cholesterol in rodents and LDL cholesterol in nonhuman primates. *Proc Natl Acad Sci USA* 105, 11915-11920.
18. Piper D, Jackson S, Liu Q, Romanow W, Shetterly S, Thibault S, Shan B, Walker N (2007). The Crystal Structure of PCSK9: A Regulator of Plasma LDL-Cholesterol. *Structure* 15, 545-552.
19. Cunningham D, Danley D E, Geoghegan K F, Matthew C Griffor M C, Hawkins J L, Subashi T A, Varghese A H, Ammirati M J, Culp J S, Hoth L R, Mansour M N, McGrath K M, Seddon A P, Shenolikar S, Stutzman-Engwall K J, Warren L C, Xia D, Qiu X (2007). Structural and biophysical studies of PCSK9 and its mutants linked to familial hypercholesterolemia. *Nature Struc Mol Biol* 14, 413-419.
20. Seidah N, Benjannet S, Wickham L, Marcinkiewicz J, Jasmin S, Stifani S, Basak A, Prat A, Chrétien M (2003). The secretory proprotein convertase neural apoptosis-regulated convertase 1 (NARC-1) liver regeneration and neuronal differentiation. *Proc Natl Acad Sci USA* 100, 928-933.
21. McNutt M C, Kwon H J, Chen C, Chen J R, Horton J D, Lagace T A (2009). Antagonism of secreted PCSK9 increases low density lipoprotein receptor expression in HepG2 cells. *J Biol Chem* 284, 10561-10570.
22. Swergold G, Biedermann S, Renard R, Nadler D, Wu R; Mellis S (2010). Safety, Lipid, and Lipoprotein Effects of REGN727/SAR236553, a Fully-Human Proprotein Convertase Subtilisin Kexin 9 (PCSK9) Monoclonal Antibody Administered Intravenously to Healthy Volunteers. *Circulation* 122, A23251.
23. Dias C, Shaywitz A, Smith B, Emery M, Bing G, Gibbs J, Wishner B, Stolman D, Crispino C, Cook B, Colbert A, Retter M, Xu R (2011). A Phase 1, Randomized, Double-Blind, Placebo-Controlled, Ascending Single Dose Study to Evaluate the Safety, Tolerability and Pharmacodynamics of AMG145. *Circulation* 124.
24. Amgen (2010) Ascending Multiple Dose Study to Evaluate the Safety, Tolerability, Pharmacokinetics and Pharmacodynamics of AMG 145 in Subjects With Hyperlipidemia on Stable Doses of a Statin. ClinicalTrails.Gov.
25. Crunkhorn S (2012). PCSK9 antibody reduces LDL cholesterol. *Nature Rev Drug Disc* 11, 11.

What is claimed is:
1. A compound of the formula:

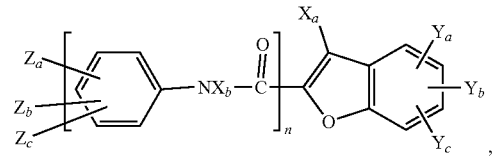

including pharmaceutically acceptable salts and stereoisomers of said compound, wherein:
$X_a$ and $X_b$ are independently selected from the group consisting of H and $CH_3$;
$Y_a$, $Y_b$ and $Y_c$ may be the same or different and are selected from the group consisting of H, halogen and $(C_1-C_3)$-alkoxy;
$Z_a$, $Z_b$ and $Z_c$ are the same or different and are selected from the group of H, $(C_1-C_3)$-alkoxy, $(C_1-C_4)$-alkyl, COOH, $CONR_{10}R_{11}$, 2-oxazole, 2-oxazoline and 2-benzoxazole; wherein $R_{10}$ and $R_{11}$ are independently selected from the group of H, optionally substituted $(C_1-C_3)$-alkyl and optionally substituted aryl; and
n=2;
wherein either:
(i) $X_a$ is methyl; one of $Y_a$, $Y_b$ and $Y_c$ is substituted at the 5-position or the 7-position of the benzofuran ring and is methoxy and the others are H; one of $Z_a$, $Z_b$ and $Z_c$ is substituted at the 4-position of the benzene ring and is selected from the group of $CONR_{10}R_{11}$, methylaminocarbonyl, branched $(C_3-C_4)$-alkyl, methoxy, 2-oxazolyl, 4,5-dihydro-oxazol-2-yl, and 2-benzoxazole substituents, and the others are H, wherein $R_{10}$ and $R_{11}$ are independently selected from the group of H, optionally substituted $(C_1-C_3)$-alkyl and optionally substituted aryl; or
(ii) $X_a$ is methyl; one of $Y_a$, $Y_b$ and $Y_c$ is substituted at the 5-position or the 7-position of the benzofuran ring and is methoxy and the others are H; one of $Z_a$, $Z_b$ and $Z_c$ is substituted at the 3-position of the benzene ring and is selected from the group of $CONR_{10}R_{11}$, methylaminocarbonyl, branched $(C_3-C_4)$-alkyl, methoxy, 2-oxazolyl, 4,5-dihydro-oxazol-2-yl, and 2-benzoxazole substituents, and the others are H, wherein $R_{10}$ and $R_{11}$ are independently selected from the group of H, optionally substituted $(C_1-C_3)$-alkyl and optionally substituted aryl.

2. The compound of claim 1, wherein $X_a$ is methyl, one of $Y_a$, $Y_b$ and $Y_c$ is substituted at the 5-position or the 7-position of the benzofuran ring and is methoxy and the others are H, one of $Z_a$, $Z_b$ and $Z_c$ is substituted at the 4-position of the benzene ring and is selected from the group of $CONR_{10}R_{11}$, methylaminocarbonyl, branched $(C_3-C_4)$-alkyl, methoxy, 2-oxazolyl, 4,5-dihydro-oxazol-2-yl, and 2-benzoxazole substituents, and the others are H, wherein $R_{10}$ and $R_{11}$ are independently selected from the group of H, optionally substituted $(C_1-C_3)$-alkyl and optionally substituted aryl.

3. The compound of claim 1, wherein $X_a$ is methyl, one of $Y_a$, $Y_b$ and $Y_c$ is substituted at the 5-position or the 7-position of the benzofuran ring and is methoxy and the others are H, one of $Z_a$, $Z_b$ and $Z_c$ is substituted at the 3-position of the benzene ring and is selected from the group of $CONR_{10}R_{11}$, methylaminocarbonyl, branched $(C_3-C_4)$-alkyl, methoxy, 2-oxazolyl, 4,5-dihydro-oxazol-2-yl, and 2-benzoxazole substituents, and the others are H, wherein $R_{10}$ and $R_{11}$ are independently selected from the group of H, optionally substituted $(C_1-C_3)$-alkyl and optionally substituted aryl.

4. A compound of the formula:

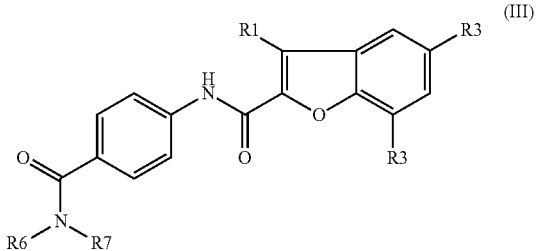

wherein: $R_1$ is selected from the group consisting of H and $CH_3$; $R_3$ is independently selected from the group consisting of H and $(C_1-C_3)$-alkoxy; one of $R_6$ and $R_7$ is H and the other is

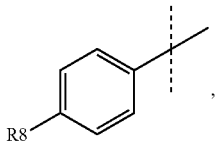

, wherein $R_8$ is selected from the group consisting of $CO_2H$, $CONHR_9$, 2-oxazole, 2-oxazoline, 2-benzoxazole; $R_9$ is H or optionally substituted $(C_1-C_3)$-alkyl; or a pharmaceutically acceptable salt or stereoisomer of the compound.

5. A compound selected from the group consisting of N—(4-{[4-(1,3-benzoxazol-2-yl)phenyl](methyl)carbamoyl}phenyl)-1-benzofuran-2-carboxamide (SBC-115,423); N—(4-{[4-(1,3-benzoxazol-2-yl)phenyl]carbamoyl}phenyl)-5-methoxy-3-methyl-1-benzofuran-2-carboxamide (SBC-115,418); N—{4-[(4-carbamoylphenyl)carbamoyl]phenyl}-1-benzofuran-2-carboxamide (SBC-115,424); N—(4-{[4-(4,5-dihydro-1,3-oxazol-2-yl)phenyl]carbamoyl} phenyl)-1-benzofuran-2-carboxamide (SBC-115,432); N—(4-{[4-(1,3-oxazol-2-yl)phenyl]carbamoyl}phenyl)-1-benzofuran-2-carboxamide (SBC-115,433); 7-methoxy-3-methyl-N—(4-{[4-(1,3-oxazol-2-yl) phenyl]carbamoy}phenyl)-1-benzofuran-2-carboxamide (SBC-115,445); and pharmaceutically acceptable salts or stereoisomers thereof.

6. The compound of claim 5, which is N—(4-{[4-(1,3-benzoxazol-2-yl)phenyl]carbamoyl}phenyl)-5-methoxy-3-methyl-1-benzofuran-2-carboxamide (SBC-115,418) or a pharmaceutically acceptable salt or stereoisomer thereof.

7. The compound of claim 5, which is N—(4-{[4-(1,3-benzoxazol-2-yl)phenyl](methyl)carbamoyl}phenyl)-1-benzofuran-2-carboxamide (SBC-115,423) or a pharmaceutically acceptable salt or stereoisomer thereof.

* * * * *